(12) United States Patent
Griffiths et al.

(10) Patent No.: US 11,723,733 B2
(45) Date of Patent: *Aug. 15, 2023

(54) LIMITED MOVEMENT OF A SURGICAL MOUNTING PLATFORM CONTROLLED BY MANUAL MOTION OF ROBOTIC ARMS

(71) Applicant: INTUITIVE SURGICAL OPERATIONS, INC., Sunnyvale, CA (US)

(72) Inventors: Paul G. Griffiths, Santa Clara, CA (US); Paul W. Mohr, Mountain View, CA (US); Nitish Swarup, Sunnyvale, CA (US); Michael Costa, Los Angeles, CA (US); David Q. Larkin, Menlo Park, CA (US); Thomas G. Cooper, Menlo Park, CA (US)

(73) Assignee: INTUITIVE SURGICAL OPERATIONS, INC., Sunnyvale, CA (US)

(*) Notice: Subject to any disclaimer, the term of this patent is extended or adjusted under 35 U.S.C. 154(b) by 114 days.

This patent is subject to a terminal disclaimer.

(21) Appl. No.: 17/321,115

(22) Filed: May 14, 2021

(65) Prior Publication Data

US 2021/0267699 A1 Sep. 2, 2021

Related U.S. Application Data

(63) Continuation of application No. 16/355,517, filed on Mar. 15, 2019, now Pat. No. 11,033,345, which is a
(Continued)

(51) Int. Cl.
*A61B 34/35* (2016.01)
*A61B 34/30* (2016.01)
(Continued)

(52) U.S. Cl.
CPC .............. *A61B 34/35* (2016.02); *A61B 34/30* (2016.02); *A61B 50/10* (2016.02); *A61B 50/18* (2016.02);
(Continued)

(58) Field of Classification Search
CPC ......... A61B 34/30; A61B 34/35; A61B 50/10; A61B 50/18; A61B 2034/304; A61B 2050/105; A61B 2017/00017
(Continued)

(56) References Cited

U.S. PATENT DOCUMENTS 5,855,583 A   1/1999  Wang et al.
6,246,200 B1  6/2001  Blumenkranz et al.
(Continued)

FOREIGN PATENT DOCUMENTS

CN   101579260 A   11/2009
JP   H07241789 A   9/1995
(Continued)

OTHER PUBLICATIONS

Extended European Search Report for Application No. 15751849.9, dated Sep. 18, 2017, 13 pages.
(Continued)

*Primary Examiner* — Atul Trivedi
(74) *Attorney, Agent, or Firm* — Artegis Law Group, LLP

(57) ABSTRACT

Techniques for limiting motion of a first structure include a manipulator supported by the first structure, a second structure supporting the first structure, and a processor. The processor is configured to, in response to entering a first mode, determine, relative to the first structure, a first position of a reference location on entry into the first mode, the reference location being associated with a link of the manipulator; and while in the first mode: detect a manual movement of the reference location to a second position
(Continued)

relative to the first structure, wherein a difference between the first and second positions comprises a displacement having first and second components in respective different first and second directions; and, in response, command the second structure to move relative to the reference location in the first direction so as to reduce the first component while not changing the second component.

20 Claims, 15 Drawing Sheets

Related U.S. Application Data continuation of application No. 15/118,305, filed as application No. PCT/US2015/016616 on Feb. 19, 2015, now Pat. No. 10,285,764.

(60) Provisional application No. 61/942,347, filed on Feb. 20, 2014.

(51) Int. Cl.
 A61B 50/10 (2016.01)
 A61B 50/18 (2016.01)
 A61B 17/00 (2006.01)

(52) U.S. Cl.
 CPC ........... *A61B 2017/00017* (2013.01); *A61B 2034/304* (2016.02); *A61B 2050/105* (2016.02)

(58) Field of Classification Search
 USPC .......................................................... 701/1
 See application file for complete search history.

(56) References Cited

U.S. PATENT DOCUMENTS

| | | | |
|---|---|---|---|
| 6,788,018 B1 | 9/2004 | Blumenkranz | |
| 8,038,108 B2 | 10/2011 | Yasunaga et al. | |
| 8,444,631 B2* | 5/2013 | Yeung | A61B 34/30 606/1 |
| 8,594,841 B2* | 11/2013 | Zhao | A61B 34/35 606/174 |
| 8,600,551 B2* | 12/2013 | Itkowitz | A61B 34/77 700/250 |
| 9,101,348 B2 | 8/2015 | Griffiths et al. | |
| 9,587,878 B2 | 3/2017 | Paydar et al. | |
| 9,795,453 B2 | 10/2017 | Tierney et al. | |
| 9,820,818 B2 | 11/2017 | Malackowski et al. | |
| 10,130,436 B2 | 11/2018 | Griffiths et al. | |
| 10,285,764 B2 | 5/2019 | Griffiths et al. | |
| 11,069,082 B1* | 7/2021 | Ebrahimi Afrouzi | G06T 7/593 |
| 2006/0074406 A1* | 4/2006 | Cooper | A61B 34/37 606/1 |
| 2007/0061735 A1 | 3/2007 | Hoffberg et al. | |
| 2007/0119274 A1* | 5/2007 | Devengenzo | A61B 34/71 74/490.01 |
| 2007/0142969 A1* | 6/2007 | Devengenzo | A61B 34/71 700/245 |
| 2009/0171371 A1* | 7/2009 | Nixon | A61B 34/37 700/264 |
| 2009/0248038 A1* | 10/2009 | Blumenkranz | A61B 34/30 606/130 |
| 2010/0225209 A1* | 9/2010 | Goldberg | G16H 20/40 312/209 |
| 2010/0228249 A1* | 9/2010 | Mohr | A61B 1/000096 715/764 |
| 2011/0082587 A1 | 4/2011 | Ziaei et al. | |
| 2012/0061155 A1 | 3/2012 | Berger et al. | |
| 2012/0173018 A1 | 7/2012 | Allen et al. | |
| 2012/0290134 A1* | 11/2012 | Zhao | A61B 34/30 901/47 |
| 2012/0310255 A1* | 12/2012 | Brisson | A61B 17/285 606/130 |
| 2013/0053866 A1 | 2/2013 | Leung et al. | |
| 2013/0096576 A1 | 4/2013 | Cooper et al. | |
| 2013/0190774 A1* | 7/2013 | Beira | A61B 34/72 606/130 |
| 2013/0224710 A1* | 8/2013 | Yang | A61B 34/30 434/262 |
| 2013/0231680 A1* | 9/2013 | Diolaiti | B25J 13/025 606/130 |
| 2013/0237766 A1 | 9/2013 | Pell et al. | |
| 2013/0245375 A1* | 9/2013 | DiMaio | A61B 34/30 600/166 |
| 2013/0304084 A1* | 11/2013 | Beira | F16H 19/08 74/89.22 |
| 2013/0325029 A1* | 12/2013 | Hourtash | A61B 34/30 606/130 |
| 2013/0325030 A1* | 12/2013 | Hourtash | B25J 9/1607 606/130 |
| 2013/0325031 A1* | 12/2013 | Schena | A61B 34/70 606/130 |
| 2013/0325032 A1* | 12/2013 | Schena | B25J 9/003 606/130 |
| 2013/0325033 A1* | 12/2013 | Schena | A61B 34/30 606/130 |
| 2013/0331858 A1* | 12/2013 | Devengenzo | A61B 46/10 901/41 |
| 2014/0018788 A1 | 1/2014 | Engelman et al. | |
| 2014/0039521 A1* | 2/2014 | Mohr | B25J 9/1689 606/130 |
| 2014/0039681 A1* | 2/2014 | Bowling | A61B 34/37 700/261 |
| 2014/0052153 A1* | 2/2014 | Griffiths | A61B 34/30 606/130 |
| 2014/0081659 A1 | 3/2014 | Nawana et al. | |
| 2014/0343570 A1 | 11/2014 | Schena et al. | |
| 2015/0223890 A1 | 8/2015 | Miller et al. | |
| 2015/0223892 A1 | 8/2015 | Miller et al. | |
| 2016/0184032 A1 | 6/2016 | Romo et al. | |
| 2017/0014998 A1 | 1/2017 | Langenfeld et al. | |
| 2017/0112583 A1 | 4/2017 | Cohen et al. | |
| 2017/0128147 A1 | 5/2017 | Bowling et al. | |
| 2017/0156803 A1 | 6/2017 | McGrogan et al. | |
| 2017/0239002 A1 | 8/2017 | Crawford et al. | |
| 2017/0296183 A1 | 10/2017 | Shelton, IV et al. | |
| 2017/0304020 A1 | 10/2017 | Ng et al. | |
| 2019/0000576 A1 | 1/2019 | Mintz et al. | |
| 2019/0105776 A1 | 4/2019 | Ho et al. | |
| 2019/0209251 A1 | 7/2019 | Griffiths et al. | |
| 2019/0282311 A1 | 9/2019 | Nowlin et al. | |
| 2019/0298465 A1* | 10/2019 | Chin | A61B 17/29 |
| 2020/0129250 A1 | 4/2020 | Kapadia et al. | |
| 2020/0129251 A1 | 4/2020 | Kapadia et al. | |
| 2020/0330174 A1* | 10/2020 | Bertram | A61B 1/000096 |
| 2021/0059766 A1* | 3/2021 | Graetzel | A61B 34/30 |
| 2021/0068909 A1* | 3/2021 | Eyre | B25J 5/007 |
| 2022/0226054 A1* | 7/2022 | Beckman | A61B 34/37 |
| 2022/0226057 A1* | 7/2022 | Beckman | A61B 34/30 |
| 2023/0073575 A1* | 3/2023 | Scheib | A61B 1/0005 |
| 2023/0075988 A1* | 3/2023 | Scheib | A61B 1/00149 |
| 2023/0076736 A1* | 3/2023 | Scheib | A61B 34/30 |
| 2023/0076998 A1* | 3/2023 | Scheib | A61B 34/76 |
| 2023/0077141 A1* | 3/2023 | Scheib | A61G 13/101 |

FOREIGN PATENT DOCUMENTS

| | | | | |
|---|---|---|---|---|
| JP | 2009525097 A | 7/2009 | | |
| JP | 2011224745 A | 11/2011 | | |
| WO | WO-9729690 A1 | 8/1997 | | |
| WO | WO-2006079108 A1 | 7/2006 | | |
| WO | WO-2006124390 A2 | 11/2006 | | |
| WO | WO-2012091814 A2 | 7/2012 | | |
| WO | WO-2014151744 A1 | 9/2014 | | |
| WO | WO-2021155026 A1 * | 8/2021 | ......... A61B 10/0233 |
| WO | WO-2021178961 A1 * | 9/2021 | ............ A61B 34/20 |
| WO | WO-2022070000 A1 * | 4/2022 | |

(56) References Cited

FOREIGN PATENT DOCUMENTS

WO     WO-2022070001 A1 *   4/2022
WO     WO-2022175851 A1 *   8/2022

OTHER PUBLICATIONS

International Search Report and Written Opinion for Application No. PCT/US2015/016616, dated Jul. 3, 2015, 11 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

LIMITED MOVEMENT OF A SURGICAL MOUNTING PLATFORM CONTROLLED BY MANUAL MOTION OF ROBOTIC ARMS

CROSS-REFERENCE TO RELATED APPLICATIONS

This application is a continuation of U.S. patent application Ser. No. 16/355,517 (filed Mar. 15, 2019), which is a continuation of U.S. patent application Ser. No. 15/118,305 (filed Aug. 11, 2016), which is the U.S. national phase of International Patent Application No. PCT/US2015/016616 (filed Feb. 19, 2015), which designated the United States and claimed right of priority to U.S. Provisional Patent Application No. 61/942,347 (filed Feb. 20, 2014). Each of which is incorporated herein by reference.

BACKGROUND

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. Because the average hospital stay for a standard surgery is typically significantly longer than the average stay for an analogous minimally invasive surgery, increased use of minimally invasive techniques could save millions of dollars in hospital costs each year. While many of the surgeries performed each year in the United States could potentially be performed in a minimally invasive manner, only a portion of the current surgeries use these advantageous techniques due to limitations in minimally invasive surgical instruments and the additional surgical training involved in mastering them.

Minimally invasive robotic surgical or telesurgical systems have been developed to increase a surgeon's dexterity and avoid some of the limitations on traditional minimally invasive techniques. (Teleoperated medical devices, such as surgical systems, are sometimes called robotic surgical systems because they incorporate robot technology). In telesurgery, the surgeon uses some form of remote control (e.g., a servomechanism or the like) to manipulate surgical instrument movements, rather than directly holding and moving the instruments by hand. In telesurgery systems, the surgeon can be provided with an image of the surgical site at a surgical workstation. While viewing a two- or three-dimensional image of the surgical site on a display, the surgeon performs the surgical procedures on the patient by manipulating master control devices, which in turn control motion of the servo-mechanically operated instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI® system commercialized by from Intuitive Surgical, Inc. of Sunnyvale, Calif.

A variety of structural arrangements can be used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. Nos. 7,594,912; 6,758,843; 6,246,200; and 5,800,423; the full disclosures of which are incorporated herein by reference. These linkages often make use of a parallelogram arrangement to hold an instrument having a shaft. Such a manipulator structure can constrain movement of the instrument so that the instrument pivots about a remote center of manipulation positioned in space along the length of the rigid shaft. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 7,763,015; 6,702,805; 6,676,669; 5,855,583; 5,808,665; 5,445,166; and 5,184,601; the full disclosures of which are incorporated herein by reference.

A variety of structural arrangements can also be used to support and position the robotic surgical manipulator and the surgical instrument at the surgical site during robotic surgery. Supporting linkage mechanisms (e.g., serial kinematic chains of two or more individual links, connected by moveable joints, and the like), sometimes referred to as set-up joints, or set-up joint arms, are often used to position and align each manipulator with the respective incision point in a patient's body. A single linkage may include two or more individual component mechanical joints (or an infinite number, in the case of a continuously flexible structure), but as a whole would be considered a single joint with two or more degrees of freedom corresponding to the individual component joints. The supporting linkage mechanism facilitates the alignment of a surgical manipulator with a desired surgical incision point and targeted anatomy. Exemplary supporting linkage mechanisms are described in U.S. Pat. Nos. 6,246,200 and 6,788,018, the full disclosures of which are incorporated herein by reference.

While the new telesurgical systems and devices have proven highly effective and advantageous, still further improvements are desirable. In general, improved minimally invasive robotic surgery systems are desirable. It would be particularly beneficial if these improved technologies enhanced the efficiency and ease of use of robotic surgical systems. For example, it would be particularly beneficial to increase maneuverability, improve space utilization in an operating room, provide a faster and easier set-up, inhibit collisions between robotic devices during use, and/or reduce the mechanical complexity and size of these new surgical systems.

BRIEF SUMMARY

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention generally provides improved robotic and/or surgical devices, systems, and methods. Kinematic linkage structures and associated control systems described herein are particularly beneficial in helping system users to arrange the robotic structure in preparation for use, including in preparation for a surgical procedure on a particular patient. Exemplary robotic surgical systems described herein may have one or more kinematic linkage sub-systems that are configured to help align a manipulator structure with the surgical work site. The joints of these set-up systems may be actively driven, passive (so that they are manually articulated and then locked into the desired configuration while the manipulator is used therapeutically), or a mix of both. Embodiments of the robotic systems described herein may employ a set-up mode in which one or more joints are actively driven in response to manual articulation of one or more other joints of the kinematic chain. In many embodiments, the actively driven joints will move a platform structure that supports multiple manipulators in response to manual movement of one of those manipulators, facilitating and expediting the arrangement of the overall system by moving those multiple manipulators as a unit into an initial orientational and/or positional alignment with the workspace. Input of the manipulator movement and independent positioning of one, some or all of the manipulators supported by the platform can optionally be provided through a passive set-up joint systems supporting one, some, or all of the manipulators relative to the platform. Optionally, manual movement of a set-up joint linkage disposed between a manipulator and the platform can result in a movement of the platform, with the platform (and the other manipulators supported thereby) following manual movement of the manipulator with a movement analogous to leading a horse by the nose.

Thus, in a first aspect, a method for preparing for robotic surgery is provided. The method includes sensing an input displacement of a first link of a first robotic manipulator from an initial position to a displaced position relative to an orienting platform, calculating a movement of a set-up structure linkage in response to the input displacement so that the first link of the first manipulator returns toward the initial position, and driving the set-up structure linkage per the calculated movement. The input displacement may result from a manual articulation of the set-up joint linkage supporting the first manipulator so that the first link moves toward a desired alignment with a surgical site. The set-up structure linkage may support the orienting platform and the orienting platform may support the first manipulator via the set-up joint linkage and a second manipulator.

In many embodiments of the method for preparing for robotic surgery, the method can include maintaining a fixed pose of the first manipulator during the input displacement so that the first manipulator moves as a substantially solid body. In this embodiment, the set-up structure may be driven while a user manually moves the first link toward the desired alignment with the surgical site.

In additional embodiments of the method for preparing for robotic surgery, the first link may have a preferred positional relationship relative to the orienting platform prior to the manual movement. The calculated movement of the set-up structure linkage may then move the orienting platform so as to return toward the preferred positional relationship during the manual movement. The preferred positional relationship may be used to help maintain a desired range of motion of the first manipulator relative to the orienting platform.

In further embodiments of the method for preparing for robotic surgery, the movement of the set-up structure linkage may be calculated using a velocity of the first link relative to the orienting platform during the input displacement. The driving of the set-up structure linkage may diminish this velocity. The method may further include reducing the velocity of the first link relative to the orienting platform by a saturation threshold when the velocity exceeds the saturation threshold. In other exemplary embodiments, the calculated movement may resiliently urge the set-up structure away from a configuration when the velocity of the first link relative to the orienting platform moves the set-up structure toward an undesirable motion-limiting configuration. In other embodiments, the driving of the setup structure may occur in a platform movement mode. The mode may be entered when the set-up linkage structure approaches or reaches an undesirable motion-limiting configuration.

In many embodiments, the method for preparing for robotic surgery may include instrument holders coupled to each of the manipulators. The manipulators may be configured to support an associated surgical instrument mounted to the instrument holder relative to a manipulator base. The manipulators may be further configured to insert the associated surgical instrument along an insertion axis into a patient through an associated remote center of manipulation (RC). Additionally, the manipulators may be configured to rotate the instrument holder around one or more axes that intersect the associated RC. Also the axes may be transverse to the insertion axis. For example, a first and second manipulator axis may intersect the associated RC, and each may be transverse to the insertion axis. Moreover the second manipulator axis may be transverse to the first manipulator axis.

In many embodiments, the set-up structure linkage may include a mounting base, a column, a member, and an extendable boom. The column may be slideably coupled with the mounting base. Additionally, the column may be selectively positioned relative to the mounting base along a first support axis that is vertically oriented. The member may be a boom base member rotationally coupled to the column through a shoulder joint. The member may be selectively oriented relative to the column around a second support axis that is vertically oriented. The extendable boom may be slideably coupled with the member to selectively position the extendable boom relative to the member along a third support axis that is horizontally oriented. The orienting platform may be rotationally coupled to the extendable boom member. In some embodiments, the first link is the instrument holder or is adjacent thereto. The calculated movement may include a movement of a plurality of joints of the set-up structure linkage and the plurality of joints may be driven per the calculated movement so that the first manipulator is well-conditioned. In other exemplary embodiments, the manual movement may align the associated first RC of the first manipulator with a desired first RC of the surgical site. The driven movement of the set-up structure linkage may move the associated RC of the second manipulator toward a second desired RC of the surgical site.

In additional embodiments, the method for preparing for robotic surgery may include a manipulator with an orienting platform movement input mounted adjacent to the first link. The movement input may normally be in a first state and manually actuatable to a second state. The orienting platform may not move in response to movement of the first link when the movement input is in the first state. Further, the method for preparing for robotic surgery may include mounting a cannula to the first manipulator after the manual movement. The cannula may provide access to an internal surgical site for a surgical instrument supported by the first manipulator. This exemplary embodiment may further include inhibiting movement of the orienting platform in response to the mounting of the cannula. The exemplary method may use joint brakes to inhibit movement along joints of the set-up structure linkage in response to the movement input being in the first state or in response to the mounting of the cannula to the first manipulator.

In a second aspect, another method for preparing for robotic surgery is provided. The method includes manually moving a first manipulator so that a first link of the manipulator moves toward a desired alignment with a surgical site, sensing an input displacement of the first link from an initial position to a displace position relative to the platform, calculating a movement of a linkage in response to the input displacement, driving the linkage per the calculated movement so that the platform follows the first link, and treating tissue at the surgical site by driving the first and second manipulators. The calculated movement may be such that the first link of the first manipulator returns toward the initial positional relationship relative to the platform. The linkage may support the platform and the platform may support the first and second manipulator.

In another aspect, a system for robotic surgery is provided. The robotic surgery system includes a platform supporting the bases of manipulators, a support structure supporting the platform and a processor coupling the manipulators to the support structure. A first and second robotic manipulator supported by the platform may have a manipulator linkage including a first link and a drive system coupled to the manipulator linkage so as to drive the first link during surgery. The support structure may include support linkage including a base and a drive system coupled to the support linkage so as to drive the platform relative to the support structure base. The processor may have a platform movement mode which calculates a set-up command in response to a manual movement of the first link of the first manipulator relative to the platform. The processor may then transmit a platform command to the support structure so as to move the platform and the manipulators.

In many exemplary embodiments of the system for robotic surgery, the processor includes non-transitory machine-readable code embodying instructions for determining an input displacement of the first link of the first manipulator from a first position to a second position relative to the platform. The input displacement may be due to the manual movement of the first link. The non-transitory machine-readable code may also embody instructions for calculating the movement command so as to affect a desired movement of the support structure using the input displacement so that the orienting platform moves while manually moving the first link.

In other exemplary embodiments, the system further includes a manually articulatable linkage disposed between the platform and the first manipulator. The processor, while in the platform movement mode, may allow manual articulation of the manually articulatable linkage and may inhibit articulation of the first manipulator. The processor may drive the support structure so that the manipulator moves as a substantially rigid body and the platform follows the first link during the manual movement of the first link.

In additional embodiments, the processor may be configured to calculate the movement of the linkage using a velocity of the first link relative to the orienting platform so that the driving of the linkage of the set-up structure reduces the relative velocity. The processor may be further configured to calculate the movement command so that the velocity of the first link relative to the orienting platform is reduced by a saturation velocity when the velocity of the first link relative to the orienting platform exceeds the saturation threshold. In further embodiments, the processor may be configured to calculate the movement command so that the movement of the set-up structure is resiliently urged away from a configuration when the velocity of the first link relative to the orienting platform moves the set-up structure toward an undesirable motion-limiting configuration of a set-up joint linkage between the manipulator and the orienting platform. The platform movement mode may be entered in response to the set-up linkage structure approaching or reaching the undesirable configuration.

In many embodiments, the system may include instrument holders coupled to each of the manipulators. The manipulators may be configured to support an associated surgical instrument mounted to the instrument holder relative to a manipulator base. The manipulators may be further configured to insert the associated surgical instrument along an insertion axis into a patient through an associated remote center of manipulation (RC). Additionally, the manipulators may be configured to rotate the instrument holder around one or more axes that intersect the associated RC. Also, the axes may be transverse to the insertion axis. For example, a first and second manipulator axis may intersect the associated RC, and each may be transverse to the insertion axis. Moreover, the second manipulator axis may be transverse to the first manipulator axis.

In many embodiments of the system, the set-up structure linkage may include a mounting base, a column, a member, and an extendable boom. The column may be slideably coupled with the mounting base. Additionally, the column may be selectively positioned relative to the mounting base along a first support axis that is vertically oriented. The member may be a boom base member rotationally coupled to the column through a shoulder joint. The member may be selectively oriented relative to the column around a second support axis that is vertically oriented. The extendable boom may be slideably coupled with the member to selectively position the extendable boom relative to the member along a third support axis that is horizontally oriented. The orienting platform may be rotationally coupled to the extendable boom member. In some embodiments, the first link is the instrument holder or is adjacent thereto. The calculated movement may include a movement of a plurality of joints of the set-up structure linkage and the plurality of joints may be driven per the calculated movement so that the first link of the first manipulator has the preferred positional relationship relative to the manipulator base.

In additional exemplary embodiments, the first manipulator of the system may include an orienting platform movement input mounted thereon or adjacent thereto. The movement input may normally be in a first state and may be manually actuatable to a second state. When the movement input is in the first state, the processor is configured to inhibit movement of the orienting platform in response to movement of the first link. The system may further include a cannula mounted to the first manipulator and the processor may be configured to inhibit movement of the orienting platform during the mounting of the cannula. In many exemplary embodiments, the support structure linkage may include a plurality of joints. The processor may be configured to inhibit movement along each joint of the set-up structure linkage with an associated joint break in response to movement input being in the first state or in response to the mounting of the cannula to the first manipulator.

In some embodiments, a method for positioning a teleoperated manipulator or other medical device system component for surgery or other medical procedure is provided. The method may include sensing an input displacement of a first link of a first robotic manipulator from an initial positional relationship relative to an orienting platform to a displaced positional relationship relative to the orienting platform. The input displacement may result from a manual articulation of a set-up joint linkage supporting the first manipulator. The input displacement may include a first displacement in a first direction, a second displacement in a second direction, and a third displacement in a third direction. The first, second, and third directions may be perpendicular to one another. The method may further include calculating a movement of a set-up structure linkage in response to the input displacement so that the first link of the first manipulator returns toward the initial positional relationship in the first direction relative to orienting platform. The calculated movement may disregard the displacement in the third direction. The set-up structure linkage may support the orienting platform and the orienting platform may support the first manipulator via the set-up joint linkage and a second manipulator. The method may further include driving the set-up structure linkage per the calculated movement in the first direction.

In some embodiments, the set-up structure linkage may be driven only in the first direction and not in the second direction or the third direction, even when the displacements in the second and third directions are within a range of motion of the set-up structure. The first direction may be a vertical z-direction. Optionally, driving may drive a translational column member to adjust a height of the orienting platform. In some embodiments the translational column member may be programmed with an upper translational limit. The method may include stopping the driving of the translational column member when the translational column member reaches the upper translational limit.

In some implementations, the driving of the set-up structure occurs in a platform movement mode. The platform movement mode may be entered in response to the set-up linkage structure reaching a range of motion limit threshold of the set-up linkage structure. The platform movement mode may be entered in response to the set-up linkage structure remaining within the range of motion limit threshold for a predetermined duration of time. The predetermined duration of time may be between 3-5 seconds. Optionally, an audio or visual alert may be provided when the set-up linkage structure reaches the range of motion limit threshold and before entering the platform movement mode. The audio or visual alert may be configured to be indicative of a time that the set-up joint has resided within the range of motion threshold to provide information on when the system will enter the orienting platform moving mode. For example, the alert may be discrete beeps for each second that the set-up joint has resided within the range of motion threshold.

In some embodiments, a system for teleoperated surgery is provided. The system may include a platform supporting the bases of the manipulators and first and second robotic manipulators supported by the platform. Each manipulator may have a manipulator linkage including a first link and a drive system operatively coupled to the manipulator linkage so as to drive the first link during surgery. The system may further include a support structure supporting the platform. The support structure may include a support linkage including a base and a drive system operatively coupled to the support linkage so as to drive the platform relative to support structure base. A processor may couple the manipulators to the support structure. The processor may have a platform movement mode. When in the platform movement mode, the processor may be configured to calculate a set-up command in response to a manual movement of the first link of the first manipulator relative to the platform. The processor may be further configured to transmit a platform movement command to the support structure so as to move the platform and the manipulators. In some embodiments, the manual movement of the first link comprises a first displacement in a first direction, a second displacement in a second direction, and a third displacement in a third direction—the first, second, and third directions being perpendicular to one another. The calculated set-up command may disregard the displacement in the third direction.

In some implementations, the platform movement command may be configured to move the support structure only in the first direction, even when the displacements in the second and third directions are within a range of motion of the set-up structure. The first direction may be a vertical z-direction. In some embodiments, the support structure may include a translational column member and the platform movement command may be configured to drive the translational column member to adjust a height of the orienting platform. In some embodiments, the translational column member may be programmed with an upper translational limit. The processor in the platform movement mode may be further configured to avoid driving the translational column member past the upper translational limit.

In some embodiments, the processor may enter the platform movement mode in response to a set-up joint linkage between the manipulator and the platform reaching a range of motion limit threshold. Optionally, the processor may enter the platform movement mode in response to the set-up joint linkage remaining within the range of motion limit threshold for a predetermined duration of time. The predetermined duration of time may be between 3-5 seconds. The processor may be further configured to provide an audio or visual alert when the set-up joint linkage reaches the range of motion limit threshold and before entering the platform movement mode. The audio or visual alert may be configured to be indicative of a time that the set-up joint has resided within the range of motion threshold to provide information on when the processor will enter the orienting platform moving mode. The alert may be discrete beeps for each second that the set-up joint has resided within the range of motion threshold.

In some embodiments, a method for preparing for teleoperated surgery is provided. The method may include sensing an input displacement of a first link of a first robotic manipulator from an initial positional relationship relative to an orienting platform to a vertically displaced positional relationship relative to the orienting platform. The input displacement may be the result of a manual articulation of a set-up joint linkage supporting the first manipulator. The input displace may include a vertical displacement in a vertical direction, a second displacement in a second direction, and a third displacement in a third direction—the vertical, second, and third directions may be perpendicular to one another. The method may further include calculating a movement of a set-up structure linkage in response to the input displacement so that the first link of the first manipulator returns toward the initial positional relationship in the vertical direction relative to orienting platform. The calculated movement may disregard the displacements in the second and third directions. The set-up structure linkage supporting the orienting platform and the orienting platform supporting the first manipulator via the set-up joint linkage and a second manipulator. The method may further include driving the set-up structure linkage per the calculated movement only in the vertical direction.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Figure 1:
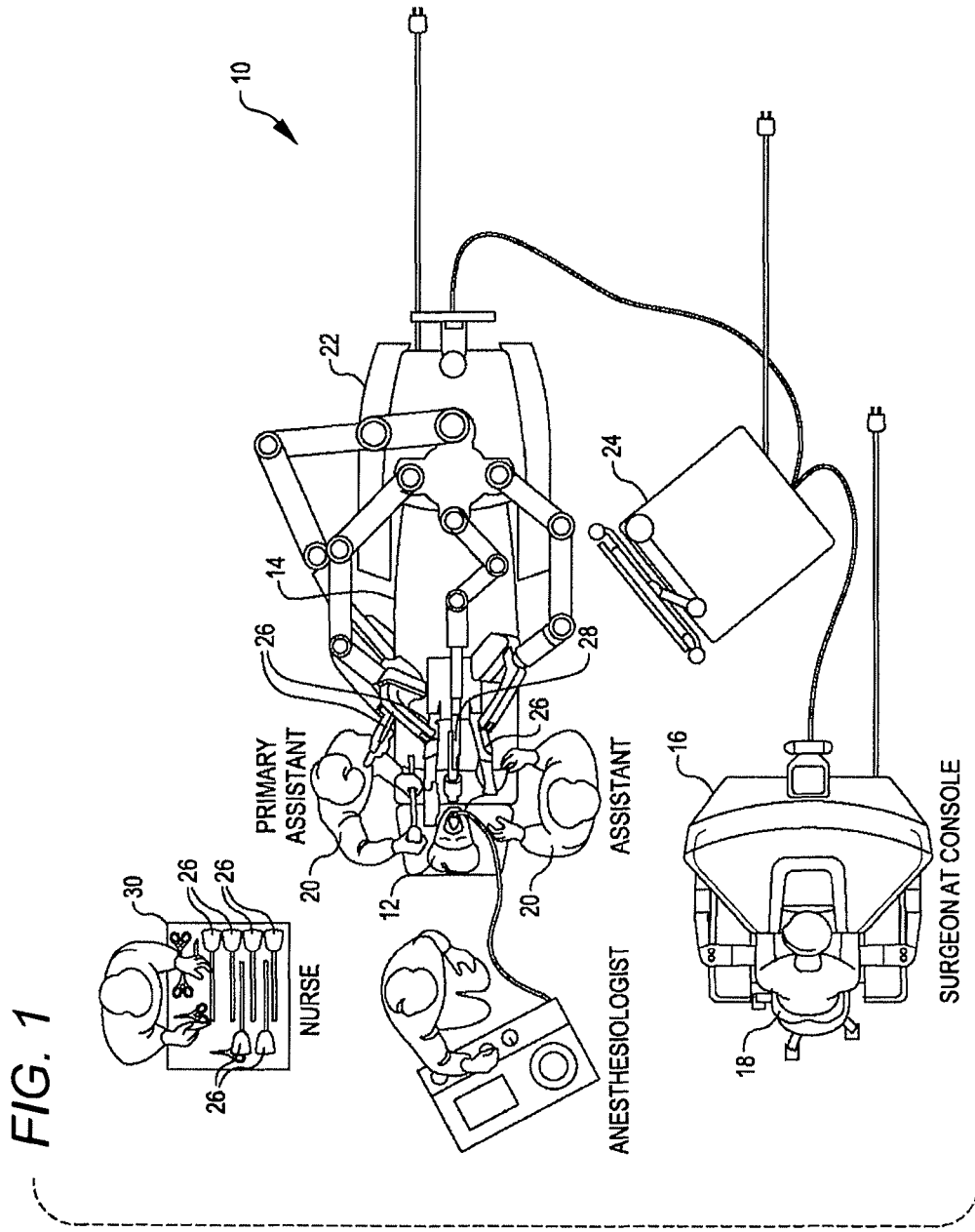
FIG. 1 is a plan view of a minimally invasive robotic surgery system being used to perform a surgery, in accordance with many embodiments.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

The kinematic linkage structures and control systems described herein are particularly beneficial in helping system users to arrange the robotic structure of a procedure on a particular patient. Along with actively driven manipulators used to interact with tissues and the like during treatment, robotic surgical systems may have one or more kinematic linkage systems that are configured to support and help align the manipulator structure with the surgical work site. These set-up systems may be actively driven or may be passive, so that they are manually articulated and then locked into the desired configuration while the manipulator is used therapeutically. The passive set-up kinematic systems may have advantages in size, weight, complexity, and cost. Unfortunately, a plurality of manipulators may be used to treat tissues of each patient, the manipulators may each independently benefit from accurate positioning so as to allow the instrument supported by that instrument to have the desired motion throughout the workspace, and minor changes in the relative locations of adjacent manipulators may have significant impact on the interactions between manipulators (with poorly positioned manipulators potentially colliding or having their range and/or ease of motion significantly reduced). Hence, the challenges of quickly arranging the robotic system in preparation for surgery can be significant.

One option is to mount multiple manipulators to a single platform, with the manipulator-supporting platform sometimes being referred to as an orienting platform. The orienting platform can be supported by an actively driven support linkage (sometimes referred to herein as a set-up structure, and typically having a set-up structure linkage, etc.) The system may also provide and control motorized axes of the robotic set-up structure supporting the orienting platform with some kind of joystick or set of buttons that would allow the user to actively drive those axes as desired in an independent fashion. This approach, while useful in some situations, may suffer from some disadvantages. Firstly, users not sufficiently familiar with robotics, kinematics, range of motion limitations and manipulator-to-manipulator collisions may find it difficult to know where to position the orienting platform in order to achieve a good setup. Secondly, the presence of any passive joints within the system means that the positioning of the device involves a combination of manual adjustment (moving the passive degrees of freedom by hand) as well as controlling the active degrees of freedom, which can be a difficult and time-consuming iterative activity.

To maintain the advantages of both manual and actively-driven positioning of the robotic manipulators, embodiments of the robotic systems described herein may employ a set-up mode in which one or more joints are actively driven in response to manual articulation of one or more other joints of the kinematic chain. In many embodiments, the actively driven joints will move a platform-supporting linkage structure that supports multiple manipulators, greatly facilitating the arrangement of the overall system by moving those manipulators as a unit into an initial orientational and/or positional alignment with the workspace. Independent positioning of one, some or all of the manipulators supported by the platform can optionally be provided through passive set-up joint systems supporting one, some, or all of the manipulators relative to the platform.

Minimally Invasive Robotic Surgery

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
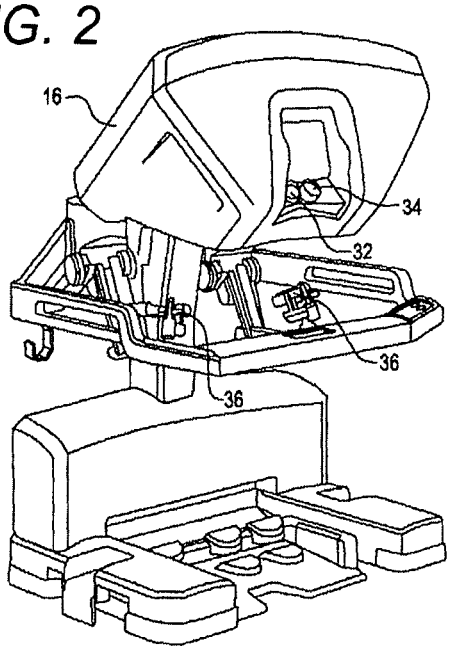
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
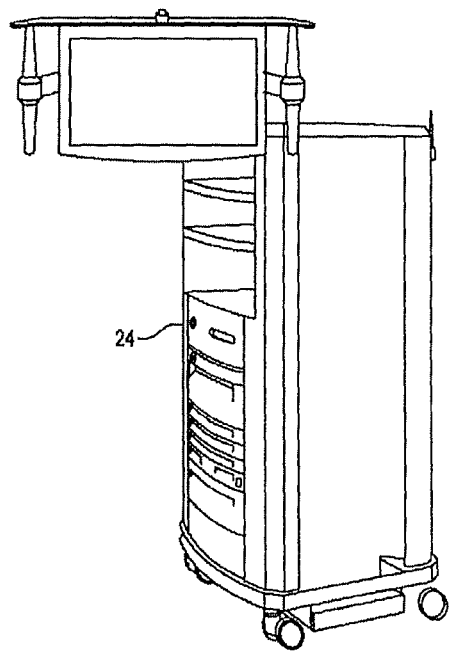
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
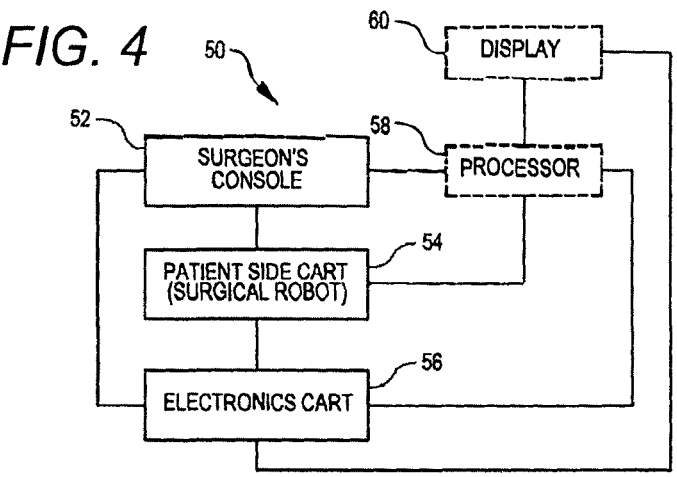
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Processor 58 will typically include a combination of hardware and software, with the software comprising tangible media embodying computer readable code instructions for performing the method steps of the control functionally described herein. The hardware typically includes one or more data processing boards, which may be co-located but will often have components distributed among the robotic structures described herein. The software will often comprise a non-volatile media, and could also comprise a monolithic code but will more typically comprise a number of subroutines, optionally running in any of a wide variety of distributed data processing architectures.

Figure 5A:
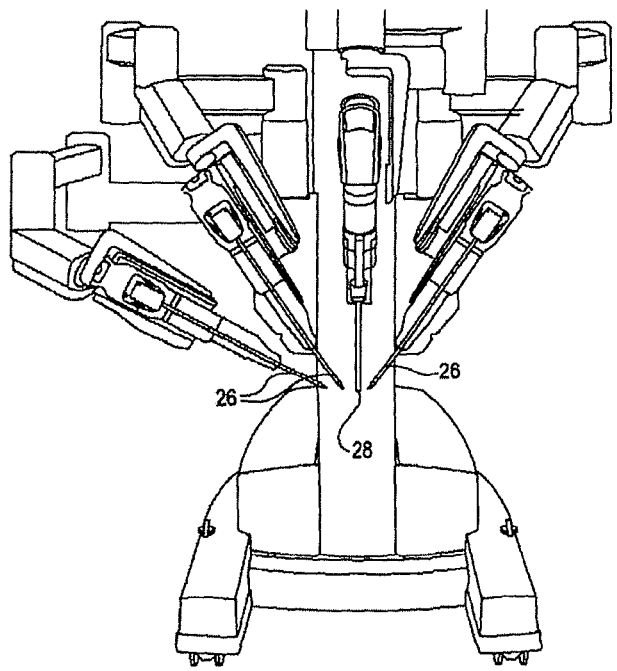
FIG. 5A is a partial view of a patient side cart (surgical robot) of a robotic surgery system, in accordance with many embodiments.
Figure 5B:
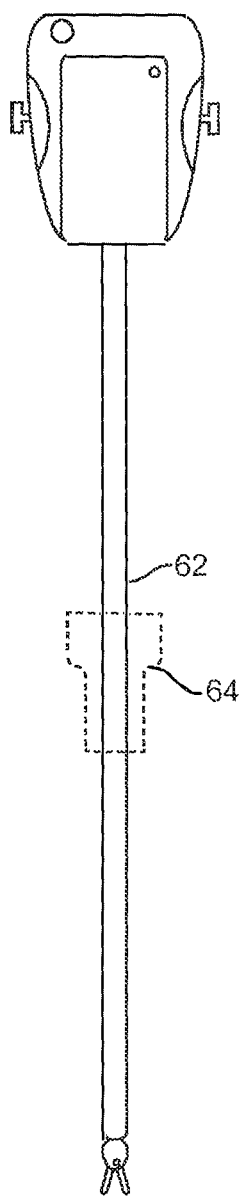
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Surgical tools 26 are inserted into the patient by inserting a tubular cannula 64 through a minimally invasive access aperture such as an incision, natural orifice, percutaneous penetration, or the like. Cannula 64 is mounted to the robotic manipulator arm and the shaft of surgical tool 26 passes through the lumen of the cannula. The manipulator arm may transmit signals indicating that the cannula has been mounted thereon.

Robotic Surgery Systems and Modular Manipulator Supports

Figure 6:
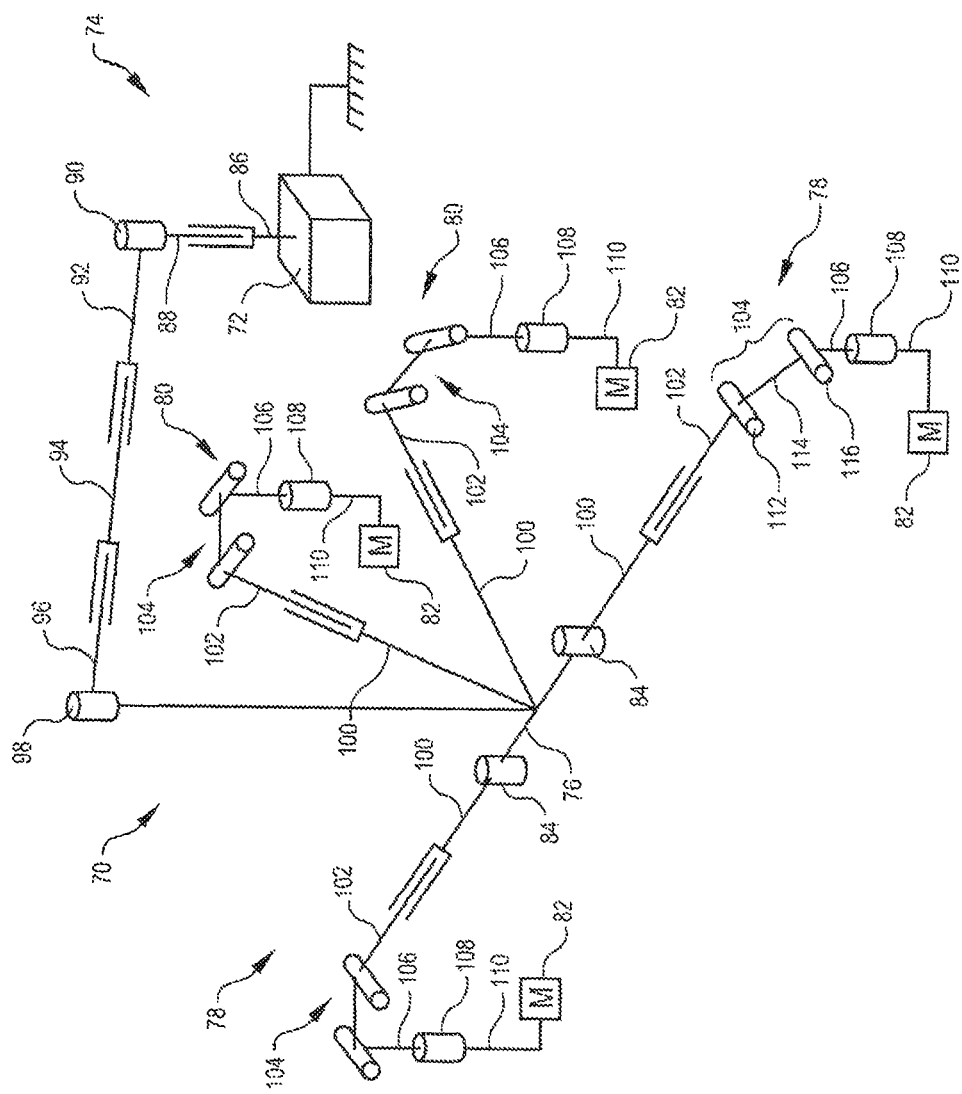
FIG. 6 is a perspective schematic representation of a robotic surgery system, in accordance with many embodiments.

FIG. 6 is a perspective schematic representation of a robotic surgery system 70, in accordance with many embodiments. The surgery system 70 includes a mounting base 72, a support linkage 74, an orienting platform 76, a plurality of outer set-up linkages 78 (two shown), a plurality of inner set-up linkages 80 (two shown), and a plurality of surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 78, 80. Each of the outer set-up linkages 78 is rotationally coupled to and supported by the orienting platform 76 by a first set-up linkage joint 84. Each of the inner set-up linkages 80 is fixedly attached to and supported by the orienting platform 76. The orienting platform 76 is rotationally coupled to and supported by the support linkage 74. And the support linkage 74 is fixedly attached to and supported by the mounting base 72.

In many embodiments, the mounting base 72 is a movable and floor supported, thereby enabling selective repositioning of the overall surgery system 70, for example, within an operating room. The mounting base 72 can include a steerable wheel assembly and/or any other suitable support features that provide for both selective repositioning as well as selectively preventing movement of the mounting base 72 from a selected position. The mounting base 72 can also have other suitable configurations, for example, a ceiling mount, fixed floor/pedestal mount, a wall mount, or an interface configured for being supported by any other suitable mounting surface.

The support linkage 74 is operable to selectively position and/or orient the orienting platform 76 relative to the mounting base 72. The support linkage 74 includes a column base 86, a translatable column member 88, a shoulder joint 90, a boom base member 92, a boom first stage member 94, a boom second stage member 96, and a wrist joint 98. The column base 86 is fixedly attached to the mounting base 72. The translatable column member 88 is slideably coupled to the column base 86 for translation relative to column base 86. In many embodiments, the translatable column member 88 translates relative to the column base 86 along a vertically oriented axis. The boom base member 92 is rotationally coupled to the translatable column member 88 by the shoulder joint 90. The shoulder joint 90 is operable to selectively orient the boom base member 92 in a horizontal plane relative to the translatable column member 88, which has a fixed angular orientation relative to the column base 86 and the mounting base 72. The boom first stage member 94 is selectively translatable relative to the boom base member 92 in a horizontal direction, which in many embodiments is aligned with both the boom base member 92 and the boom first stage member 94. The boom second stage member 96 is likewise selectively translatable relative to the boom first stage member 94 in a horizontal direction, which in many embodiments is aligned with the boom first stage member 94 and the boom second stage member 96. Accordingly, the support linkage 74 is operable to selectively set the distance between the shoulder joint 90 and the distal end of the boom second stage member 96. The wrist joint 98 rotationally couples the distal end of the boom second stage member 96 to the orienting platform 76. The wrist joint 98 is operable to selectively set the angular orientation of the orienting platform 76 relative to the mounting base 72.

Each of the set-up linkages 78, 80 is operable to selectively position and/or orient the associated manipulator 82 relative to the orienting platform 76. Each of the set-up linkages 78, 80 includes a set-up linkage base link 100, a set-up linkage extension link 102, a set-up linkage parallelogram linkage portion 104, a set-up linkage vertical link 106, a second set-up linkage joint 108, and a manipulator support link 110. In each of the set-up linkage base links 100 of the outer set-up linkages 78 can be selectively oriented relative to the orienting platform 76 via the operation of the a first set-up linkage joint 84. In the embodiment shown, each of the set-up linkage base links 100 of the inner set-up linkages 80 is fixedly attached to the orienting platform 76. Each of the inner set-up linkages 80 can also be rotationally attached to the orienting platform 76 similar to the outer set-up linkages via an additional first set-up linkage joints 84. Each of the set-up linkage extension links 102 is translatable relative to the associated set-up linkage base link 100 in a horizontal direction, which in many embodiments is aligned with the associated set-up linkage base link and the set-up linkage extension link 102. Each of the set-up linkage parallelogram linkage portions 104 configured and operable to selectively translate the set-up linkage vertical link 106 in a vertical direction while keeping the set-up linkage vertical link 106 vertically oriented. In example embodiments, each of the set-up linkage parallelogram linkage portions 104 includes a first parallelogram joint 112, a coupling link 114, and a second parallelogram 116. The first parallelogram joint 112 rotationally couples the coupling link 114 to the set-up linkage extension link 102. The second parallelogram joint 116 rotationally couples the set-up linkage vertical link 106 to the coupling link 114. The first parallelogram joint 112 is rotationally tied to the second parallelogram joint 116 such that rotation of the coupling link 114 relative to the set-up linkage extension link 102 is matched by a counteracting rotation of the set-up linkage vertical link 106 relative to the coupling link 114 so as to maintain the set-up linkage vertical link 106 vertically oriented while the set-up linkage vertical link 106 is selectively translated vertically. The second set-up linkage joint 108 is operable to selectively orient the manipulator support link 110 relative to the set-up linkage vertical link 106, thereby selectively orienting the associated attached manipulator 82 relative to the set-up linkage vertical link 106.

Figure 7:
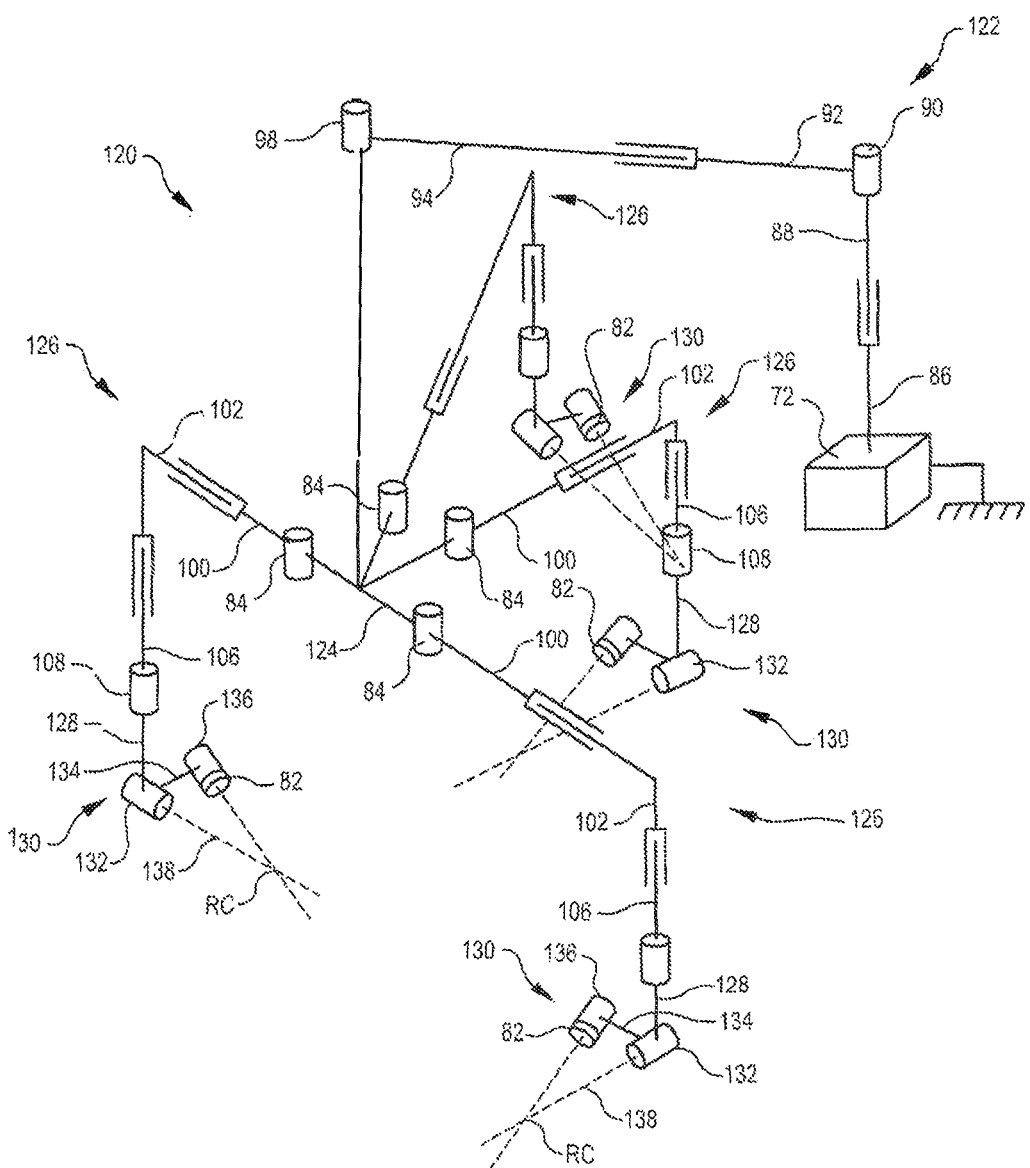
FIG. 7 is a perspective schematic representation of another robotic surgery system, in accordance with many embodiments.

FIG. 7 is a perspective schematic representation of a robotic surgery system 120, in accordance with many embodiments. Because the surgery system 120 includes components similar to components of the surgery system 70 of FIG. 6, the same reference numbers are used for similar components and the corresponding description of the similar components set forth above is applicable to the surgery system 120 and is omitted here to avoid repetition. The surgery system 120 includes the mounting base 72, a support linkage 122, an orienting platform 124, a plurality of set-up linkages 126 (four shown), and a plurality of the surgical instrument manipulators 82. Each of the manipulators 82 is operable to selectively articulate a surgical instrument mounted to the manipulator 82 and insertable into a patient along an insertion axis. Each of the manipulators 82 is attached to and supported by one of the set-up linkages 126. Each of the set-up linkages 126 is rotationally coupled to and supported by the orienting platform 124 by the first set-up linkage joint 84. The orienting platform 124 is rotationally coupled to and supported by the support linkage 122. And the support linkage 122 is fixedly attached to and supported by the mounting base 72.

The support linkage 122 is operable to selectively position and/or orient the orienting platform 124 relative to the mounting base 72. The support linkage 122 includes the column base 86, the translatable column member 88, the shoulder joint 90, the boom base member 92, the boom first stage member 94, and the wrist joint 98. The support linkage 122 is operable to selectively set the distance between the shoulder joint 90 and the distal end of the boom first stage member 94. The wrist joint 98 rotationally couples the distal end of the boom first stage member 94 to the orienting platform 124. The wrist joint 98 is operable to selectively set the angular orientation of the orienting platform 124 relative to the mounting base 72.

Each of the set-up linkages 126 is operable to selectively position and/or orient the associated manipulator 82 relative to the orienting platform 124. Each of the set-up linkages 126 includes the set-up linkage base link 100, the set-up linkage extension link 102, the set-up linkage vertical link 106, the second set-up linkage joint 108, a tornado mechanism support link 128, and a tornado mechanism 130. Each of the set-up linkage base links 100 of the set-up linkages 126 can be selectively oriented relative to the orienting platform 124 via the operation of the associated first set-up linkage joint 84. Each of the set-up linkage vertical links 106 is selectively translatable in a vertical direction relative to the associated set-up linkage extension link 102. The second set-up linkage joint 108 is operable to selectively orient the tornado mechanism support link 128 relative to the set-up linkage vertical link 106

Each of the tornado mechanisms 130 includes a tornado joint 132, a coupling link 134, and a manipulator support 136. The coupling link 134 fixedly couples the manipulator support 136 to the tornado joint 132. The tornado joint 130 is operable to rotate the manipulator support 136 relative to the tornado mechanism support link 128 around a tornado axis 136. The tornado mechanism 128 is configured to position and orient the manipulator support 134 such that the remote center of manipulation (RC) of the manipulator 82 is intersected by the tornado axis 136. Accordingly, operation of the tornado joint 132 can be used to reorient the associated manipulator 82 relative to the patient without moving the associated remote center of manipulation (RC) relative to the patient.

Figure 8:
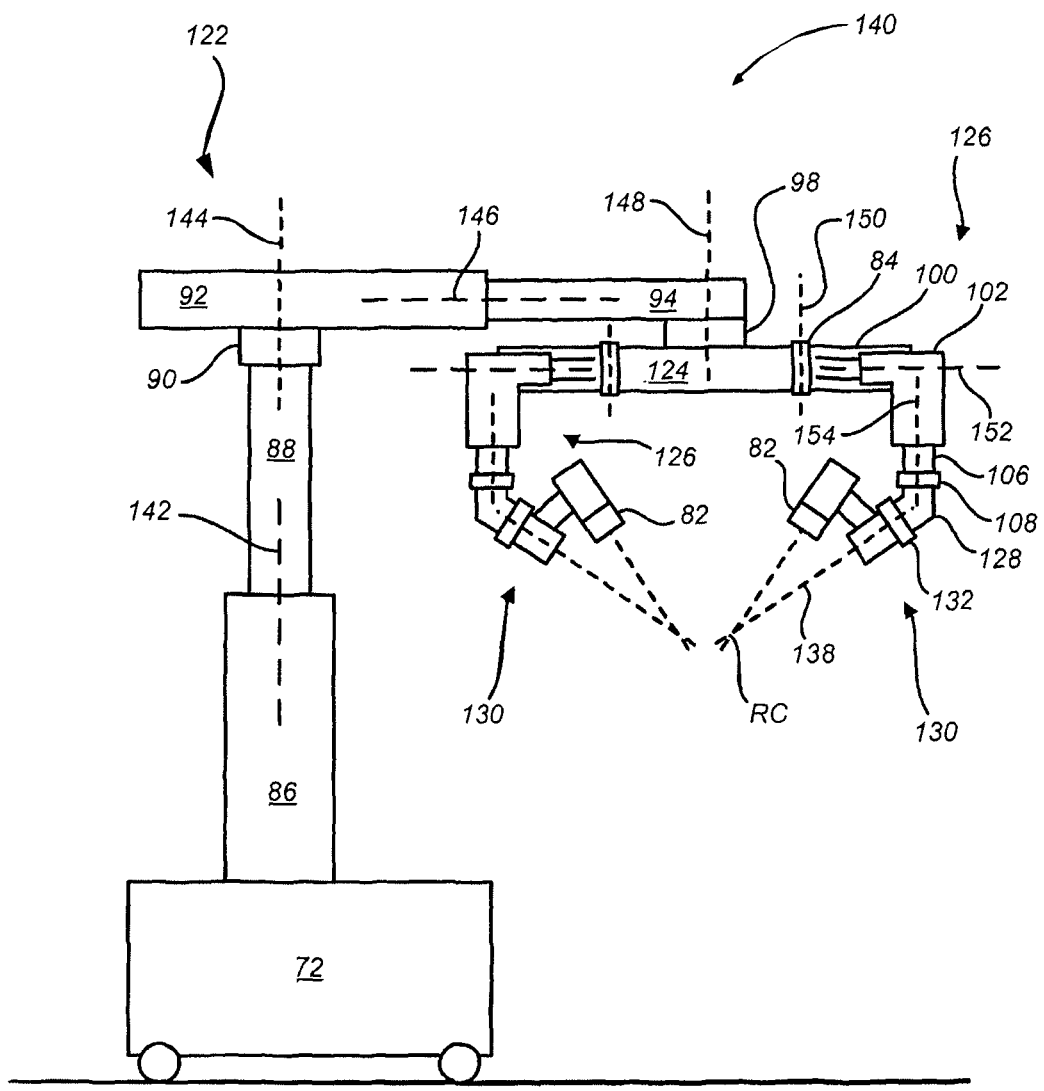
FIG. 8 shows a robotic surgery system, in accordance with many embodiments, in conformance with the schematic representation of FIG. 7.

FIG. 8 is a simplified representation of a robotic surgery system 140, in accordance with many embodiments, in conformance with the schematic representation of the robotic surgery system 120 of FIG. 7. Because the surgery system 140 conforms to the robotic surgery system 120 of FIG. 7, the same reference numbers are used for analogous components and the corresponding description of the analogous components set forth above is applicable to the surgery system 140 and is omitted here to avoid repetition.

The support linkage 122 is configured to selectively position and orient the orienting platform 124 relative to the mounting base 72 via relative movement between links of the support linkage 122 along multiple set-up structure axes. The translatable column member 88 is selectively repositionable relative to the column base 86 along a first set-up structure (SUS) axis 142, which is vertically oriented in many embodiments. The shoulder joint 90 is operable to selectively orient the boom base member 92 relative to the translatable column member 88 around a second SUS axis 144, which is vertically oriented in many embodiments. The boom first stage member 94 is selectively repositionable relative to the boom base member 92 along a third SUS axis 146, which is horizontally oriented in many embodiments. And the wrist joint 98 is operable to selectively orient the orienting platform 124 relative to the boom first stage member 94 around a fourth SUS axis 148, which is vertically oriented in many embodiments.

Each of the set-up linkages 126 is configured to selectively position and orient the associated manipulator 82 relative to the orienting platform 124 via relative movement between links of the set-up linkage 126 along multiple set-up joint (SUJ) axes. Each of the first set-up linkage joint 84 is operable to selectively orient the associated set-up linkage base link 100 relative to the orienting platform 124 around a first SUJ axis 150, which in many embodiments is vertically oriented. Each of the set-up linkage extension links 102 can be selectively repositioned relative to the associated set-up linkage base link 10 along a second SUJ axis 152, which is horizontally oriented in many embodiments. Each of the set-up linkage vertical links 106 can be selectively repositioned relative to the associated set-up linkage extension link 102 along a third SUJ axis 154, which is vertically oriented in many embodiments. Each of the second set-up linkage joints 108 is operable to selectively orient the tornado mechanism support link 128 relative to the set-up linkage vertical link 106 around the third SUJ axis 154. Each of the tornado joints 132 is operable to rotate the associated manipulator 82 around the associated tornado axis 138.

Figure 9:
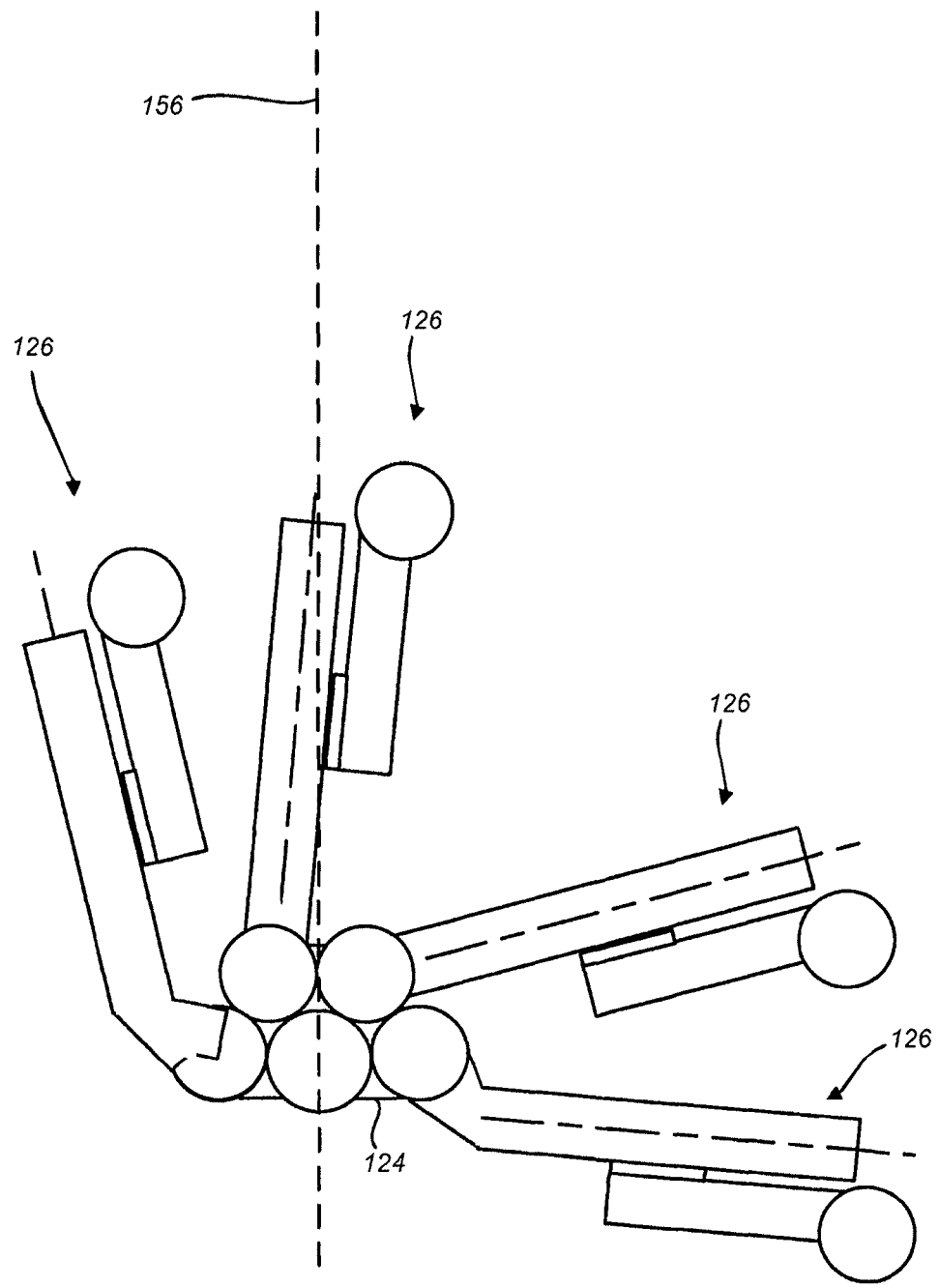
FIG. 9 illustrates rotational orientation limits of set-up linkages relative to an orienting platform of the robotic surgery system of FIG. 8.

FIG. 9 illustrates rotational orientation limits of the set-up linkages 126 relative to the orienting platform 124, in accordance with many embodiments. Each of the set-up linkages 126 is shown in a clockwise limit orientation relative to the orienting platform 124. A corresponding counter-clockwise limit orientation is represented by a mirror image of FIG. 9 relative to a vertically-oriented mirror plane. As illustrated, each of the two inner set-up linkages 126 can be oriented from 5 degrees from a vertical reference 156 in one direction to 75 degrees from the vertical reference 156 in the opposite direction. And as illustrated, each of the two outer set-up linkages can be oriented from 15 degrees to 95 degrees from the vertical reference 156 in a corresponding direction.

Figure 10:
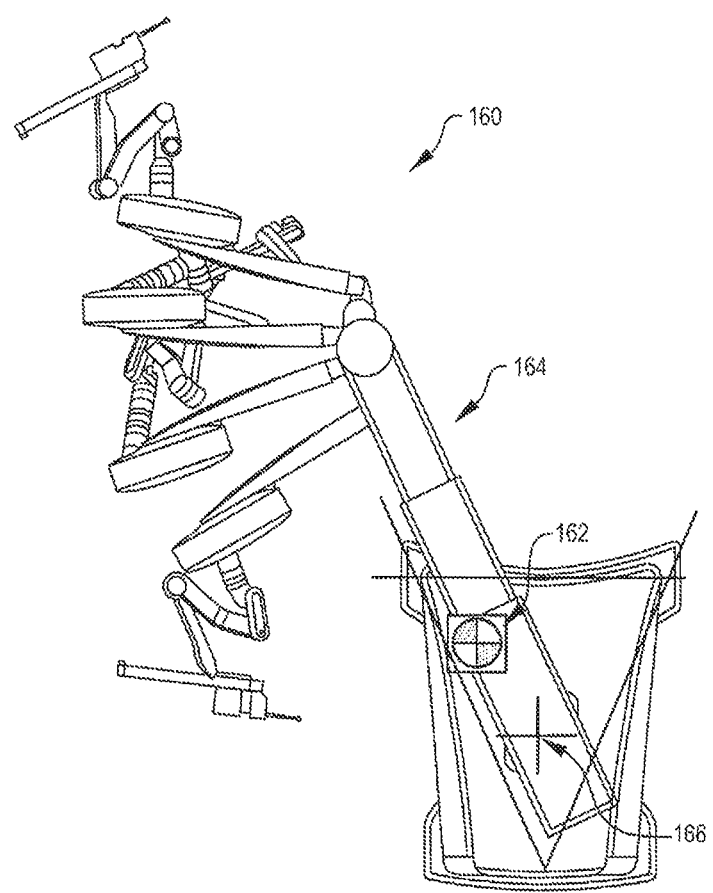
FIG. 10 shows a center of gravity diagram associated with a rotational limit of the boom assembly for a robotic surgery system, in accordance with many embodiments.

FIG. 10 shows a center of gravity diagram associated with a rotational limit of a support linkage for a robotic surgery system 160, in accordance with many embodiments. With components of the robotic surgery system 160 positioned and oriented to shift the center-of-gravity 162 of the robotic surgery system 160 to a maximum extent to one side relative to a support linkage 164 of the surgery system 160, a shoulder joint of the support linkage 164 can be configured to limit rotation of the support structure 164 around a set-up structure (SUS) shoulder-joint axis 166 to prevent exceeding a predetermined stability limit of the mounting base.

Figure 11:
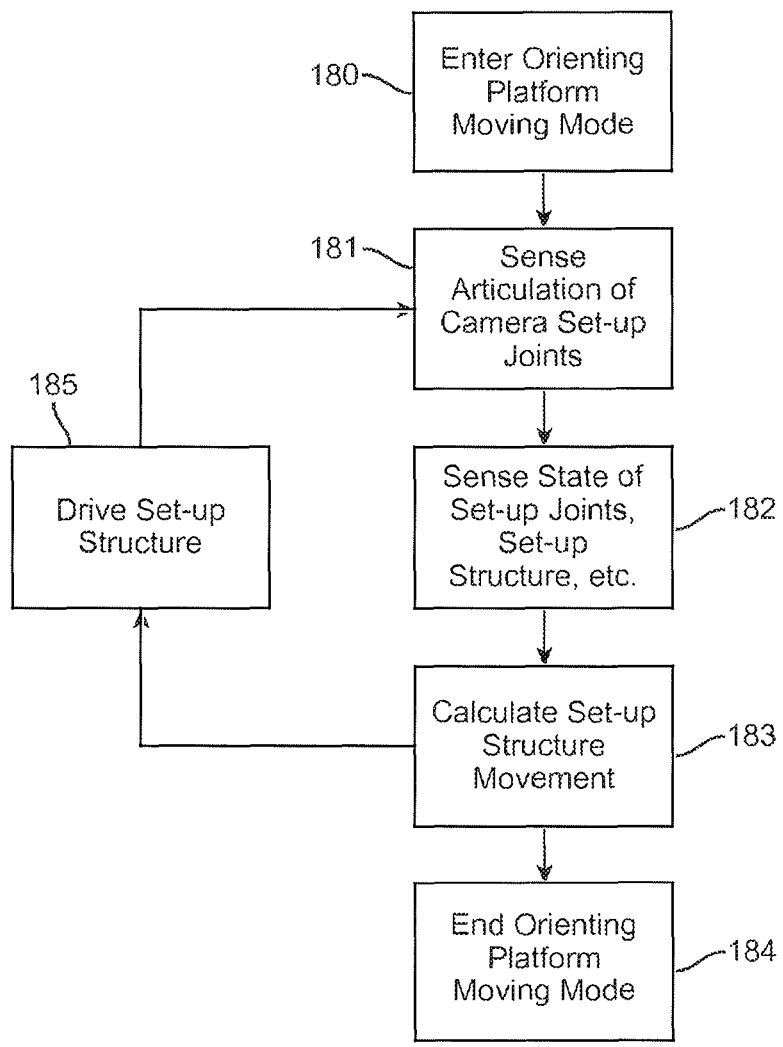
FIG. 11 is a flow chart schematically illustrating a method for preparing a robotic surgical system for surgery by driving an orienting platform in response to movement of a link of one of a plurality of robotic manipulator arms supported by the orienting platform.
Figure 12:
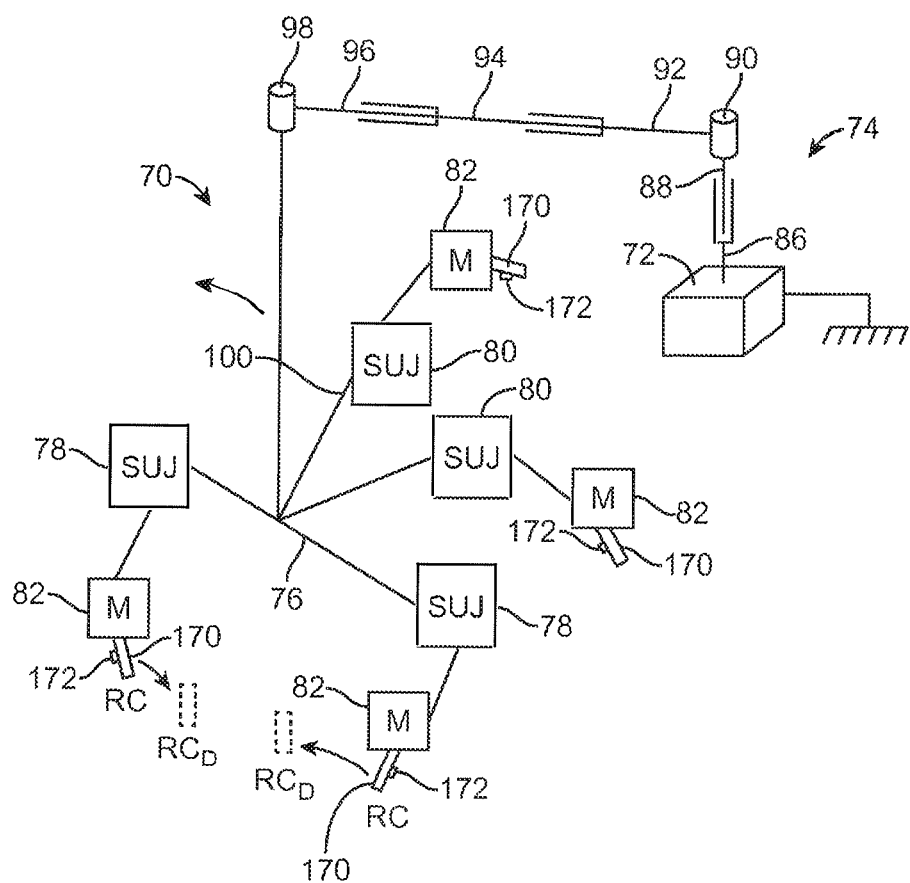
FIG. 12 is a perspective schematic representation of movement of an orienting platform supported by a cart-mounted set-up support structure so as to provide a desired alignment of a plurality of manipulator arms with associated surgical access sites.

Positioning of the Orienting Platform in Response to Manual Articulation of One or More Joints of the Kinematic Chain Supported by the Orienting Platform FIGS. 11 and 12 schematically illustrate a method for driving the orienting platform in response to movement of a link 170 of a manipulator 82 or a link of a set-up joint linkage during set-up of the robotic system for use. In exemplary embodiments, the reference location for movement may not be located on link 170, but may instead be offset relative to link 170. For example, the reference location for movement may be disposed at a remote center location offset from a base (or other structure) of a manipulator linkage, particularly where that manipulator mechanically constrains motion of the manipulator to spherical motion at a fixed remote center location relative to that base. Hence, while the base (or other linkage structure) of the manipulator may serve as an input link 170, the reference location may be spatially separated from the link itself, often at a fixed location in the frame of reference of the link. Optionally, the input link may be a link of a set-up joint linkage 78, 80 configured to support a manipulator 82 relative to the orienting platform 76. For the sake of simplicity, implementations are described below as using movement of link 170 of a manipulator 82 as input. It should be understood however, that in many embodiments, an input link may be a link of a set-up joint linkage 78, 80.

Prior to driving of the orienting platform, the platform will have an initial position and orientation relative to mounting base 72 (depending on the states of the joints of the support linkage 70), and the manipulators will each have an associated location and orientation relative to the orienting platform (depending on the states of the joints of the set-up linkages 78, 80). Similarly, a link 170 of each of the manipulators 82 (and/or a reference location associated with that link) will have a position and orientation relative to the platform 76 which depends on the state of the joints of the manipulator and set-up linkages between the manipulator base (schematically illustrated here by the boxes M) and the platform 76. Link 170 will typically comprise a base of the manipulator, but may alternatively comprise a link kinematically near or adjacent the surgical instrument, such as the instrument holder or carriage. The joint states of the manipulator can generally be described by a pose vector θ.

During set-up, it will often be desirable to move one, some, or all of the links 170 from their initial positions and orientations to desired position(s) and orientation(s) aligned with a surgical site. Additionally, it will often be desirable to start a surgical procedure with the manipulators in a well-conditioned state so as to provide the surgeon with a wide range of motion, help avoid singularities, and the like. In other words, for a given manipulator it will be beneficial to provide both a desired alignment between link 170 and the surgical worksite (including having the remote center RC of the manipulator at or near a desired access site location RCD), and to have the manipulator at or near a desired manipulator state or pose OD. Note that the manipulator may already be at or near the desired manipulator pose prior to movement of link 170, or that may be in an initial pose $\theta_I$ significantly different than the desired, well-conditioned pose ($\theta_I \neq \theta_D$). Appropriate positioning and configuring of the manipulators relative to each other may also help avoid manipulator collisions. Where the manipulator is not in a well-conditioned pose prior to alignment with the surgical site, the pose of the manipulator may optionally be altered to a well-conditioned pose before moving the orienting platform, after moving the orienting platform, or while moving the orienting platform. Altering the pose from the initial pose to the well-conditioned pose may be done by manually articulating the joints of the manipulator. Alternatively, there may be advantages to driving the manipulator from the initial pose toward and/or to the well-conditioned pose. For simplicity, the description below assumes the manipulators are in a desired and/or well-conditioned pose prior to initiation of movement of the platform. Regardless, mounting of multiple manipulators 82 to a common platform 76 and driven movement of that platform in response to movement of a link of one of the joints supporting one of the manipulators relative to the platform can facilitate movement of the manipulators into the desired alignment with the surgical space.

The joints of the manipulator will often be maintained in a fixed configuration during movement of the orienting platform and/or manual articulation of the set-up linkages, optionally by driving the motors of each of the joints of the manipulator so as to counteract any manual articulation, by fixing the joint states of the manipulators with joint brakes, by a combination of both, or the like. Hence, while there may be some slight flexing of the links and minor excursions of the joints during movement of the orienting platform and manual articulation of the set-up linkages, the manipulators will typically move as a substantially rigid body. Moreover, the link 170 manipulated by the user and/or to be used as a reference for movement may be any one or more link of (or even kinematically adjacent to) the manipulator or an associated set-up linkage.

Referring now to FIGS. 11 and 12, to enter the orienting platform moving mode 180 of the robotic system processor, an input 172 on or adjacent an associated link 170 may be activated. While Input 172 may optionally comprise a simple dedicated input button or the like, some embodiments may benefit from alternative user interface approaches. As an example, an exemplary input may avoid a dedicated button by instead entering the platform moving mode in response to a set-up joint operation. More specifically, the platform moving mode may be entered by first releasing the set-up joints supporting an associate manipulator so as to allow the remote center (or "port") location of that manipulator to be manually repositioned, a manual movement mode which is sometimes referred to as port clutching. When the manipulator is manually moved to within a threshold of (or in some embodiments actually reaches) a range of motion limit for the released set-up joint linkage, the system may in response enter the platform following mode. Hence, reaching (or approaching) the range of motion limit of the set-up joints becomes a method to request and/or input activation for the entering of the platform movement mode. Input 172 may alternatively be a simple normally off input.

The processor may not enter the orienting platform moving mode despite actuation of the input if a cannula is mounted to the manipulator (or to any other manipulator supported by the orienting platform). While input 172 of a given manipulator 82 is actuated, and/or in response to actuation of input 172, the set-up linkages 78, 80 disposed between that manipulator and the orienting platform will often be unlocked so as to allow manual articulation. This articulation of set-up linkages 78, 80 can be sensed and used as an input for driving the joints of the set-up structure for moving the orienting platform 76. The system will often be balanced about the axes of the set-up linkages so that the user can easily re-orient and/or re-position the manipulator relative to the operating platform in platform, with the manipulator typically moving as a relatively rigid when link 172 is moved relative to the platform and the base 72 of the system. Note that the drive system of the manipulator may be energized and controlled by the processor so as to resist articulation of the joints of the manipulator displacement, or that joint brakes of the manipulator may inhibit articulation, but that some flexing of the manipulator linkages and/or minor excursions of the joints states may still result from the forces imposed on link 172. Note also that in alternative embodiments the joints that are allowed to articulate between link 172 and the orienting platform are powered (such as in a software-center system) those joints may be energized to as to provide movement resistance forces that are sufficiently light so as to allow the link to be manually moved sufficiently for the joint state sensing system of the manipulator to readily identify the desired displacement vector for use as a desired movement input or command from the system user.

Referring still to FIGS. 11 and 12 and as generally noted above, once the orienting platform moving mode has been entered with a particular manipulator 82 to be used as the input device (such as by depressing a switch of input 172), link 170 of that manipulator can be manually moved relative to the platform. Typically, one or more (optionally all) of the set-up joints may be released so as to allow the input movement of link 170 to occur via manual articulation of the released set-up joint(s), optionally while articulation of the linkage of the manipulator is inhibited (such as by driving the manipulator to avoid movement, using a brake system of the manipulator, or the like). Hence, the input may be sensed at least in part as an articulation of one or more joints of the set-up joint system. Still further options may be employed, such as allowing the manual input via a selective combination of articulation of one or more joints of the manipulator and one or more joints of the set-up joint system. Regardless, to facilitate kinematic analysis, provide input for helpful transformations, and the like, the joint states of the set-up structure (including the joints supporting the orienting platform), the set-up joint system, and the manipulator will typically be sensed 182.

Based on the manual input command by the user (as entered by manual movement of link 170 and as sensed via the manual articulation of the joints supporting that link), commands are calculated to move the set-up structure 183. The orienting platform will often be driven per the calculated commands while the user continues to move link 170, so that the base of the manipulators supported by the orienting platform follow the manually moving link. While moving a first manipulator into a desired alignment with the surgical site, the other manipulators may each remain in a fixed pose. Similarly, any set-up linkages between the orienting platform and those other manipulators may also remain locked (and/or otherwise have their articulation inhibited) during movement of the platform. As articulation may be inhibited for all the joints between the links 170 of the other manipulators and the orienting platform, all those other input links (and other structures of the manipulators) follow link 170 of the manipulator for which input 172 is actuated.

The orienting platform may be driven so that the input set-up linkages supporting the input manipulator (for which input 172 is actuated), while the user holds and moves the associated link 170 to a desired alignment with the workspace, are urged to remain in their initial configuration (as per when the system entered the orienting platform mode). The position of the link 170 may continue to be controlled manually by the user during the movement of the orienting platform. In other words, the orienting platform can be moved so that given a current pose θ of the set-up linkages 78, 80 and a current location of the input link 170 (both during movement of the orienting platform), the drive system of the orienting platform moves the orienting platform 185 so that the input set-up linkages 78, 80 are articulated from the current pose toward their initial pose (θ→θi). The effect of this movement of the orienting platform is to largely maintain the initial spatial relationship between the input link 170 and the orienting platform, so that the orienting platform (and all the manipulators supported thereby) follows the input link as it is moved by the hand of the user. The orienting platform movement mode can be terminated 184 by releasing input 172, by mounting a cannula to the input manipulator, or the like. Note that the cannula may not be mounted to the manipulator until after the cannula extends into the patient body, so that it may be desirable for the processor system to inhibit entering of the orienting platform movement mode in response to actuation of input 172 of a manipulator to which the cannula is mounted.

In some implementations of the above method, the orienting platform range of motion may be limited to a subset (e.g., x and y, or z only, etc.) of the full range of motion (e.g., x, y, z, θ). Limiting the range of motion to a subset of the full range of motion may make system set-up more intuitive and quicker for users by reducing the DOFs involved. For example, in some situations, it may be advantageous if the orienting platform movement is limited to vertical positioning movements using the translational column member 82. This may be particularly useful for raising of a teleoperated surgical system over a patient and lowering of the system into a desired position over the patient.

In such embodiments, orienting platform moving mode may be entered 180 for example by manually moving a vertical set-up joint to or near its range of motion (ROM) limit. In some implementations, a ROM limit threshold may be defined so that the platform moving mode is entered when the vertical set-up joint is moved near a ROM limit. Optionally, the moving mode may be entered by moving a vertical set-up joint to or near its ROM limit and/or by a dedicated input button. For example, user may actuate a port clutch input to release the set-up joints to allow free movement of the set-up joints. If the user desires to raise the system, the user may manually move a vertical set-up joint to or near an upper ROM limit to enter the orienting platform moving mode 180. After entering the orienting platform moving mode 180, manual movement of the vertical set-up joint to or near the upper ROM limit may be sensed 181 and set-up structure (e.g., a translational column member 82) movement may be calculated 183 based on sensed states of the set-up joints and set-up structures. The set-up structure (e.g., a translational column member 82) may then be driven (raised) 185 per the calculation. Once there is enough clearance to position the system over the patient, the user may then need to lower the orienting platform of teleoperated system to a height where the manipulators can be positioned in their desired positions. To do so, the user may reverse the sequence of actions (e.g., manually move the vertical set-up joint to or near a lower ROM limit and lead the platform lower in height by lowering the translational column member 82).

While the above implementation is discussed as limiting motion to only the vertical orientation, it should be understood that in some embodiments the motion may be limited to other subsets of the full range of motion. In some embodiments, when a manipulator or a set-up joint is manually moved to or near a ROM limit, the system may first wait a threshold duration of time before entering the orienting platform moving mode 180. The threshold duration of time may avoid inadvertent movement of the orienting platform by manual movement of manipulators or set-up joints by a user. The threshold duration may be for example, 5 seconds or less. In some embodiments, a threshold duration may be 3 seconds. Further, it may be advantageous to provide an audio or visual indicator/alert to a user prior to entering the orienting platform moving mode. For example an audio alert may trigger when a user manually moves the set-up joint to or near a ROM limit. Optionally, the audio or visual alert may be configured indicate a duration of time that the set-up joint has resided at or near the ROM limit to provide the user information on when the system will enter the orienting platform moving mode. For example, an audio indicator may provide a countdown or discrete beeps for each second.

In some embodiments, one or more joints of the set-up structure may be programmed with upper limits to their respective range of motion. The upper limits may be programmed into one or more of the set-up structure joints due to room constraints. For example, in some situations, it may be beneficial to program a translational column member 82 with an upper limit when room ceiling heights limit the full range of motion of a translational column member 82. Optionally, when a set-up structure joint is so limited, the motion of the orienting platform during the orienting platform moving mode may similarly be limited. For example, when raising an orienting platform by manually moving a vertical set-up joint to the upper ROM limit, the system may limit the orienting platform from being raised further if the translational column member 82 reaches a preprogrammed upper limit. While some embodiments may prevent set-up structure motion beyond a programmed limit during orienting platform movement in the orienting platform moving mode, other embodiments may be provided where the movement of the orienting platform due to manual movement of a manipulator or set-up joint by a user may override a programmed limit to range of motion of a set-up structure.

Orienting platform 76 may support manipulators 80, 82 in beneficial relative positions for many procedures. Hence, once a link 170 of a first manipulator 80 has been moved to a desired alignment with a surgical worksite, the instrument holders and the like of the other manipulators will often be at or near associated desired initial alignment for their associated surgical tools, and only limited additional repositioning of the manipulators may be warranted. Minor adjustments to a particular manipulator alignment may be accommodated by releasing a brake system of the set-up joint arm supporting that manipulator relative to the orienting platform and moving that manipulator as desired relative to all the other manipulators. For example, once a camera manipulator is used to position the orienting platform and to initially align all the instrument manipulators, the set-up linkages between each instrument manipulator and the orienting platform can be released and the released manipulator position can be adjusted independently if needed. In an exemplary embodiment of orienting platform movement mode, sensing of the manual movement of a first input link 170 effectively senses movement of the manipulator from an initial remote center RC to a desired remote center RCd. Movement of the orienting platform moves the remote centers RC of the other manipulators toward their associated desired remote centers RCd. Additional adjustment of those other remote center locations can then be performed by sequentially releasing each of the set-up linkages of the associated manipulator and moving the released manipulator so as to provide the desired alignment between the released manipulator RC and the desired remote center RCd.

Calculation of the Orienting Platform Movement Commands

Figure 12A:
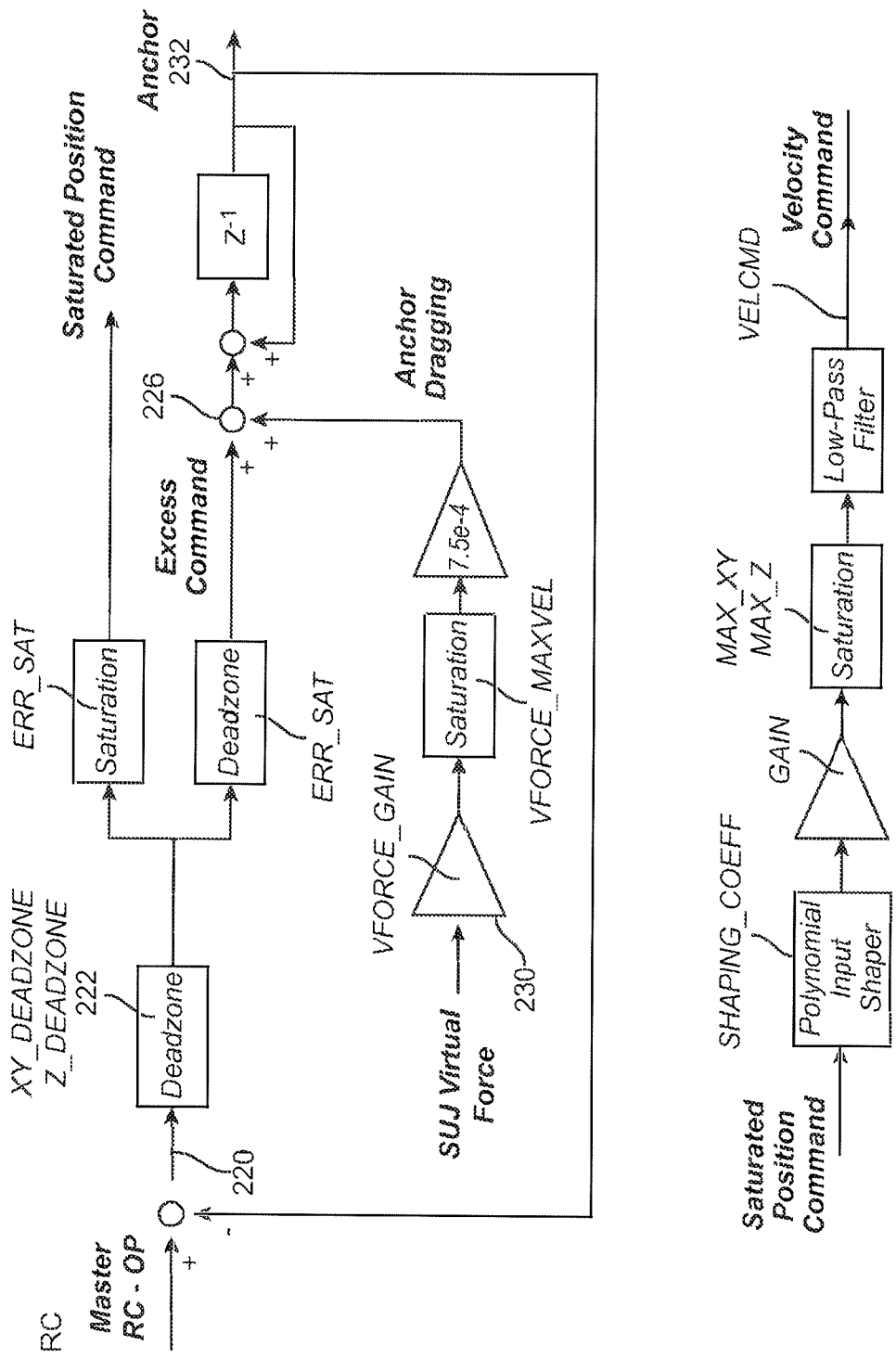
FIGS. 12A and 12B are block diagrams illustrating controllers used as components of the orienting platform drive system, and particularly showing an exemplary software system arrangement of the processor.
Figure 12B:
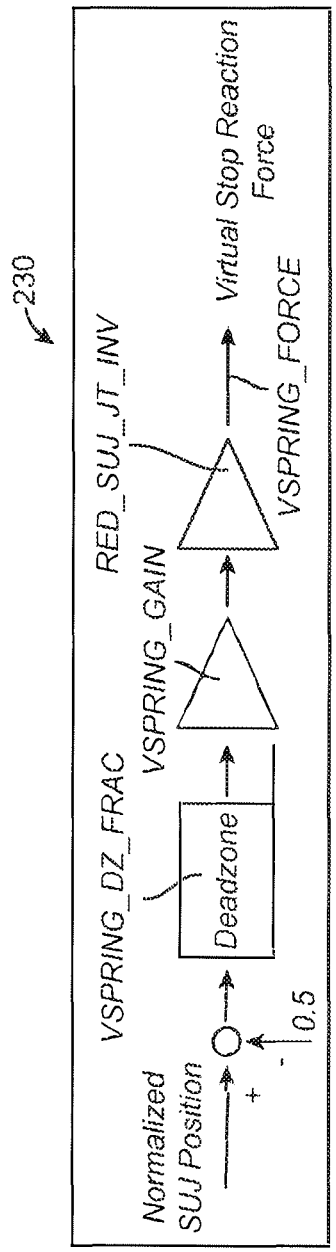

Referring now to FIGS. 12A and 12B, an exemplary software structure and/or processor arrangement for calculating the movement commands of the orienting platform can be understood. As the orienting platform and other manipulators will often follow the movement of the input link 170 for which the orienting movement input 172 has been actuated, the overall movement is somewhat analogous to (and is sometimes referred to herein as) a "Lead-the-Horse-By-the-Nose" (LHBN) control mode. The LHBN control mode allows the user to move the operating platform 76 and drive the setup-structure by manually moving the remote center of a floating manipulator 82. In a basic form, the control objective is to move the operating platform 76 such that the manipulator 82 remote-center remains at a desired location in the operating platform 76 frame. Thus, when the user manually displaces the manipulator 82 in the world frame, the controller can move the operating platform 76 and its frame through the same displacement to drive the error between the actual remote center and the desired remote center to zero.

The raw error between the actual remote center RC and desired remote center RCd locations form the input command 220 to the LHBN controller, as shown in FIG. 12A. A small dead zone 222 (less than 10 cm, often about 3 cm or less) is applied to the error signal before scaling the error into a raw velocity command. A low-pass filter (of between about 0.1 Hz and 10 Hz, typically approximately 1 Hz) generates a band-limited velocity command. The command is then saturated 224 to create the velocity command in the operating platform frame. When LHBN mode is entered a half cosine shaped scaling is applied to the command over a short window to ramp up the command in a smooth manner. Similarly, the command is scaled by a half cosine shaped scaling in the reverse direction when the mode is exited to smooth the deceleration. The velocity command, after startup/shutdown scaling, is provided to the setup structure's inverse kinematics. Further trimming of the velocity command may occur in the inverse kinematics calculations when joints are at or near (within a few their limits.

The desired remote center location RCd, also referred to herein as the anchor, is established when LHBN control mode is entered. When the LHBN control mode is initiated, the desired remote center RCd and actual remote center RC are co-located, thus starting the mode with zero error (so that the platform will not move unless and until the input link 170 moves relative to the orienting platform). Manual movement of the link 170 while in the LHBN control mode causes the platform to be driven so that the actual remote center RC generally remains at the desired remote center RCd in the frame of the operating platform. Several enhancements to the basic LHBN operation may optionally slide or alter the location of the anchor or desired remote center RCd relative to the actual remote center to tweak the behavior. The anchor can, for example, be moved by commanding an anchor dragging velocity and integrating as indicated in FIG. 12A. One anchor velocity input may be the difference between the saturated and unsaturated velocity command 226. The purpose of this feature may be to avoid large saturated velocity commands. Once the velocity command reaches saturation, any additional input motion of the remote center drags the anchor (or moves the RCd relative to the orienting platform) to keep the command just at the saturation limit. Intuitively, the error between the anchor and the remote center can be visualized as a ball, and dragging the anchor means dragging the ball's center around whenever the error vector reaches the ball's radius.

Motion away from range of motion limitations or hard stops of set-up linkages 78, 80 is also achieved through anchor dragging, as can be understood with reference to the block diagram model shown in FIG. 12B. Some automatic motion of the set-up structure 74 away from hardstops is desirable as the user may not otherwise be able to easily manually command the desired set-up structure motion. In one embodiment, a subroutine may compute a virtual force 230 acting on the platform 76 that mimics springs installed at the limits of motion of the set-up linkages 78, 80. The force can be referred to as a port-dragging force. A virtual force may be transmitted from each configured manipulator 82 to enable the setup structure controller to back away from setup joint range of motion limits. The LHBN control mode software can scale the port-dragging virtual force from the input manipulator 82 and add this quantity to the anchor dragging velocity. The effect is to create a command 232 to drive the set-up structure 76 to move away from hardstops of set-up linkages 78, 80.

Some or all of the gains, saturations, and/or deadzones used in the LHBN control mode are optionally tunable. For example, in some embodiments, the platform range of motion may be limited to a subset of the full range of motion when the platform is moved in a platform movement mode. As described above, such methods and systems may make system set-up more intuitive and quicker for users by reducing the DOFs involved. In such an embodiment, the gains for some of the directions may be tuned to zero. For example, in embodiments where only platform vertical movement is controlled during a platform movement mode, the gains for an x-direction movement and a y-direction movement may be set to zero so that only z-direction movement data is provided. Each parameter in FIGS. 12A and 12B is listed in the following Table:

Thus a large gain on the virtual force will drive the error significantly into saturation. For more description of the kernel keys involved in the calculation of the virtual force, see the Table above.

Figure 12C:
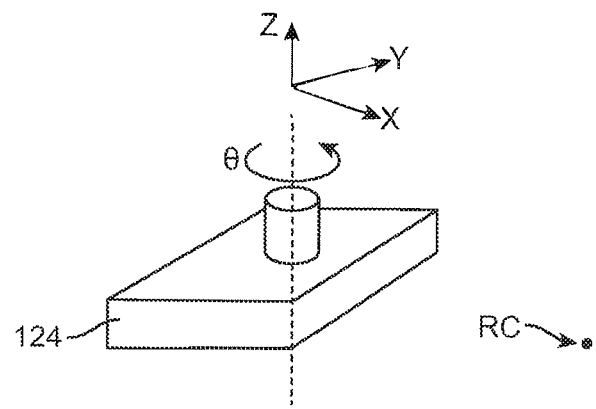
FIGS. 12C and 12D are a schematic representation of an orienting platform showing an associated coordinate system and degrees of freedom; and a perspective representation of an orienting platform supported by a ceiling gantry set-up support structure so as to provide a desired alignment of a single manipulator arm with an associated surgical access site.

Referring now to FIG. 12C, an alternative drive system for the set-up structure and orienting platform 124 preferably allows movement along x, y, and z axes to drive a manipulator RC to a desired position relative to the orienting platform. By manually moving one or more link of a manipulator 82 in space (and optionally by moving the entire manipulator), the user can cause the operating platform to follow by just computing the error vector between the desired manipulator RC position (in the orienting platform frame of reference) to the actual manipulator RC position and using this vector to generate desired x, y, z velocities.

Figure 12D:
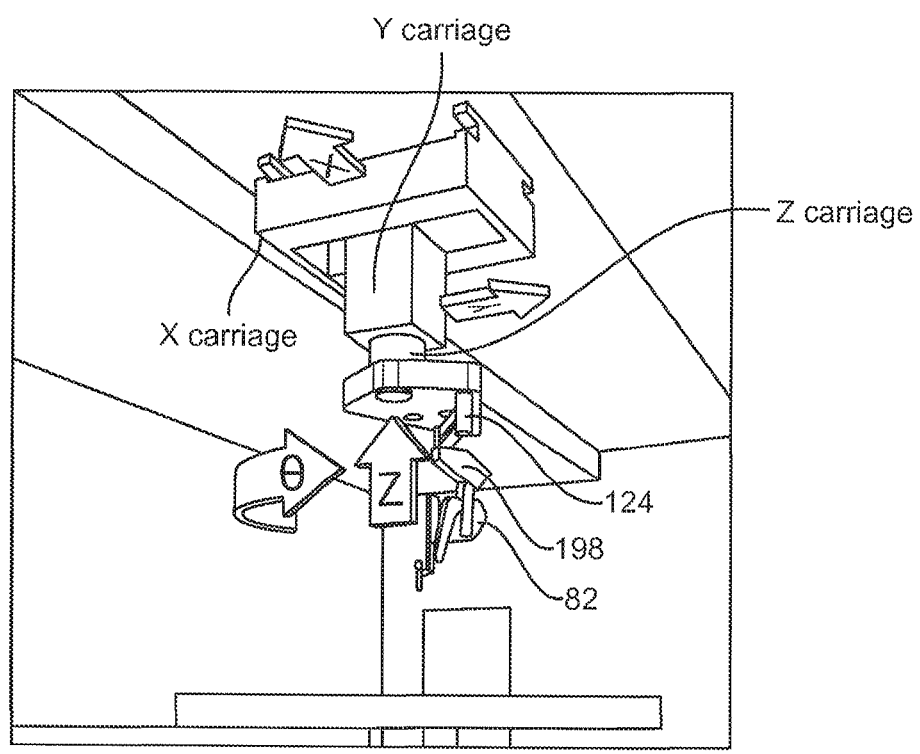

Referring now to FIGS. 12C and 12D, methods for moving the x, y, z, and θ axes of the orienting platform will generally seek to achieve a desired positioning of the orienting platform 124 and one or more manipulators 82 mounted thereon so as to provide a well-conditioned manipulator pose when starting a surgical procedure (with the various degrees of the freedom of the manipulator being desirably near their centers of range of motions while the tool is in a desired location of the surgical workspace, with the manipulator kinematics being well away from motion-inhibiting singularities, and the like). Along with orienting platforms supported by cart-mounted set-up structures such as those described above, ceiling mounted set-up structures 190 and other driven robotic linkages with one, two, three, four, or more degrees of freedom may be employed. Similarly, the input for motion may optionally be input by manually articulating a passive joint (such as one of the joints along the set-up joint structure described above)

TABLE

XY_DEADZONE, Deadzone applied to input motion in the x-y plane
Z_DEADZONE, Deadzone applied to input motion in the z direction
ERR_SAT, Maximum error input. Error beyond this value is saturated
VFORCE_GAIN, Scaling of virtual forces from setup joints into anchor dragging velocity
VFORCE_MAXVEL, Saturation of anchor dragging velocity
SHAPING_COEFF, Coefficients of the polynomial that shapes the saturated position command
GAIN, Gain from position command (error signal post deadzone and saturation) and the LBHN velocity command
MAX_XY, Maximum velocity command in the xy plane
MAX_Z, Maximum velocity command in the z direction
VELCMD, Final velocity command
VSPRING_DZ_FRAC, Deadzone fraction of each setup joint range of motion
VSPRING_GAIN, Gain from position to virtual joint force outside the deadzone of each joint
RED_SUJ_JT_INV, Inverse transpose of the setup joint Jacobian.
VSPRINT_FORCE, Final virtual force reflected to the OP The virtual spring force used to move the set-up structure linkage away from set-up joint linkage hard stops can be calculated as shown in FIG. 12B, and the deadzone fraction may determine how much of the range of motion produces no virtual force. Note that the deadzone fraction should be less than unity and that the active portion may be split evenly between the two hardstops on each joint. If the user moves the remote center such that a setup joint is against a hard-stop, anchor dragging can be used to integrate the virtual force and increase the velocity command to move away from the hard-stop. A smoothly increasing velocity command will be generated that moves the setup structure away from the from the setup joint range of motion limit. The velocity command will increase until saturation is reached at which point a steady-state velocity of the setup structure will be maintained.

and/or one or more actively driven joints (such as a joint of the manipulator 80, 82). Hence, while the systems may be described with reference to a few exemplary robotic kinematic structures, the control techniques may apply well to a range of other robotic systems having redundant degrees of freedom and/or large numbers of joints, and are particularly interesting when considering such systems that have a mix of active and passive joints; systems with one set of joints that are driven during set-up and another different set (with or without some overlapping members) of joints that are driven during surgery; systems in which individual manipulator controllers exchange only limited state information; and the like.

To use the robotic capabilities of the system during set-up, the processor of the robotic system may include software implementing a mode in which the robotic structure is driven toward and/or maintains a desired relationship or pose between the orienting platform and the manipulator remote center during manual movement of a link of the manipulator. This algorithm, when active, takes as its inputs the actual and desired relationships between the orienting platform and the manipulator remote center and drives the actual pose to the desired one, optionally without disturbing the position and orientation of the manipulator remote center. In other words, as the user moves the passive axes around, the active axes may optionally follow in such a way so as to achieve or maintain a specific robot pose.

Figure 13:
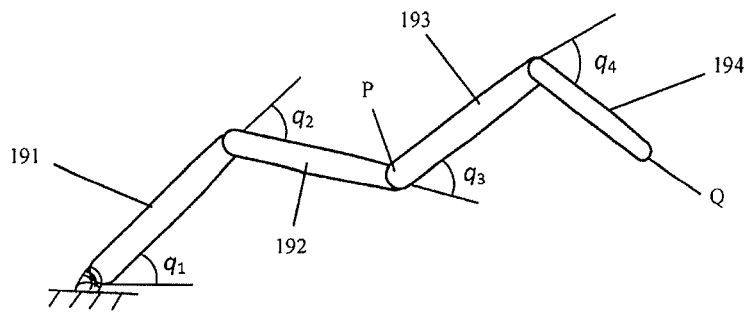
FIG. 13 schematically shows a simplified four joint planar passive/active robotic kinematic system in which active joints are driven in response to deflection of passive joints.

The simplified 4-link manipulator shown in FIG. 13 helps to explain one embodiment of the control structures and methods described herein. In this schematic manipulator, links 191 and 192 are active, meaning that $q_1$ and $q_2$ are controlled by a controller, while links 193 and 194 are passive, and can be moved by hand. Point Q is a point on the robot of direct interest to the user, and is positioned manually to a user-specified target location relative to the robot base. Hence, point Q may correspond to the remote center of the manipulator, and the user would typically position point Q so that the manipulator could, for example, be connected to the camera cannula, which may already be installed in the patient or which may be inserted in the patient after the robotic structure is moved into position. For various reasons (including maximizing usable range of motion, minimizing collisions, etc.) it is often desirable to obtain a specific relationship between P and Q. As long as joints $q_3$ and $q_4$ are free, and there is sufficient range of motion and the manipulator is not near a singularity, P can translate independently of Q, so the controller is free to establish the desired relationship if Q is simply held fixed relative to the base. This principle can be taken advantage of to automatically establish the P to Q relationship while the user holds Q fixed in space. It is also possible to continuously run this automatic positioning algorithm, so that as a user manually adjusts the position of Q, the active axes $q_1$ and $q_2$ move in such a way so as to maintain the desired P-Q relationship.

In the simplified example of FIG. 13, two active and two passive degrees of freedom are shown, and the only quantities of interest were the relative positions in the plane of P and Q. Ceiling and/or cart mounted robotic surgical systems will often be more complex: there are seven active degrees of freedom (four on the gantry and three relevant axes on the ECM) in the embodiment of FIG. 12D, and three passive axes (schematically shown by the set-up joints 198 between the orienting platform 124 and the manipulator 82), for a total of ten degrees of freedom. Maintaining the manipulator remote center end point location and orientation is often a six DOF issue, which leaves us with four extra degrees of freedom (DOFs) with which to perform our internal optimizations in this embodiment. Note that for purposes of this discussion, the exact nature of what is considered desired may include any number of criteria, and many concept described here can be applied regardless of the method used to determine the optimal target location. One strategy for performing this sort of optimization is to consider the entire system as a single 10 DOF redundant manipulator. One can then use a technique of imposing a primary, inviolable goal paired with a desired auxiliary goal of minimizing a cost function. The primary goal in our case may be to maintain the position and orientation of the manipulator remote center relative to the room and the auxiliary goal may be to achieve the optimal relationship between the orienting platform and the manipulator.

A second strategy is to segment the problem into two parts:

1) A set-up structure optimization problem that seeks to minimize a cost function. This cost function is configured to achieve a minimum when the orienting platform position and orientation reaches an optimal or desired location relative to the manipulator RC.

2) A manipulator regulation problem that seeks to maintain a constant manipulator orientation relative to the room. This second strategy benefits from the fact that the only information that needs to be shared between the ECM and Gantry manipulator is the location of the base and tip of each—it is not required to know the position of every joint. This lends this particular strategy a nice advantage in that it requires less communication bandwidth between manipulators.

Figure 14:
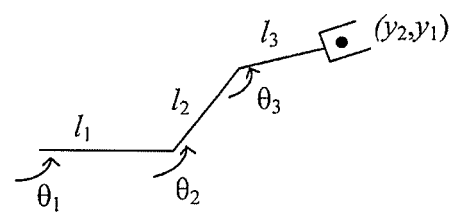
FIG. 14 schematically shows a simplified three link planar joint system for use in describing kinematic analysis of the desired joint control.
Figure 15:
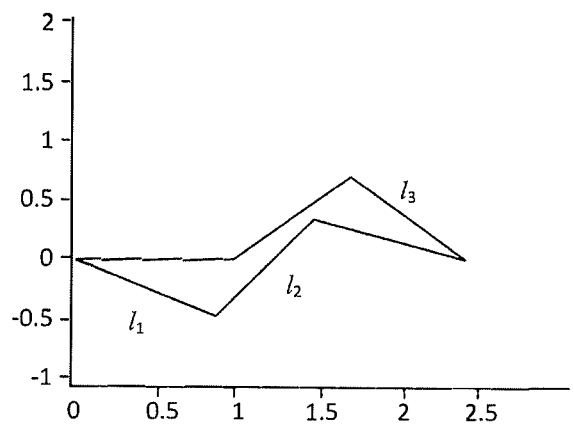
FIG. 15 graphically shows movement of a simplified planar kinematic system through its null space so as to demonstrate driven motion of a set-up structure supporting a manually articulatable joint system in response to manual articulation of one or more of those joints.

We now provide the mathematical framework necessary to move the setup structure without moving the remote center. Referring now to FIGS. 14 and 15, reconfiguring a simplified planar set-up structure linkage to a desired pose may be modeled as moving the manipulator through its null space (per the description above of FIG. 13, so that Q remains invarient while P is driven to a desired x and y location in space). Mathematically, where the lengths of links 1-3 FIG. 14 are $l_{1-3}$, the Jacobian matrix and joint position vector q can be identified as:

$$x = l_1 c_1 + l_2 c_{12} + l_3 c_{123}$$

$$y = l_1 c_1 + l_2 s_{12} + l_3 s_{123}$$

$$J = \begin{bmatrix} -s_1 - s_{12} - s_{123} & -s_{12} - s_{123} & -s_{123} \\ c_1 + c_{12} + c_{123} & c_{12} + c_{123} & c_{123} \end{bmatrix}$$

$$q = \begin{bmatrix} \theta_1 \\ \theta_2 \\ \theta_3 \end{bmatrix},$$

The following is a decomposition of the joint velocities as a sum of end-effector motion and internal joint motions that result in no end-effector motion.

$$\dot{q} = \underbrace{J^t \vec{v}}_{\substack{\text{Desired} \\ \text{Cartesian} \\ \text{motion}}} + \underbrace{(I - J^t J)\dot{\vec{q}}}_{\substack{\text{Desired internal} \\ \text{motion through Null} \\ \text{Space of manipulator}}}$$

Set $\vec{v} = [\vec{0}] \rightarrow$ meaning, we do not want end effector to move $$\text{Set } \dot{\vec{q}}_0 = \begin{bmatrix} \dot{q}_{\theta_1} \\ 0 \\ 0 \end{bmatrix} \rightarrow$$

meaning: move $\theta_1$ at velocity $\vec{q}_{\theta_1}$.

Don't care what $\theta_2$ and $\theta_3$ do, as long as these internal motions do no move end effector Hence, we can move $\theta_1$ and did not have to specify $\theta_2$ and $\theta_3$ to move the manipulator through the null space without changing end effector position. Similarly from a Matlab simulation, we see that we can move an axis through the Null space without having to specify the other joints. While the proceeding demonstrates optimization of planar set-up joints, the framework extends to orientation.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A system comprising:
    a first structure;
    a manipulator supported by the first structure;
    a second structure supporting the first structure; and
    a processor coupled to the manipulator and to the second structure;
    wherein the processor is configured to:
        in response to entering a first mode, determine, relative to the first structure, a first position of a reference location at a time of entry into the first mode, the reference location being associated with a link of the manipulator; and
        while in the first mode:
            detect a manual movement of the reference location to a second position relative to the first structure, wherein a difference between the first position and the second position comprises a displacement having at least a first displacement component in a first direction and a second displacement component in a second direction, the second direction different from the first direction,
            calculate, in response to the detected manual movement and based on at least the first displacement component, a motion of the second structure that reduces the first displacement component while not changing the second displacement component by causing the first structure to move relative to the reference location in the first direction, and
            command the second structure to move in accordance with the calculated motion.

2. The system of claim 1, wherein the first direction is orthogonal to the second direction.

3. The system of claim 1, wherein the first direction is a vertical direction of the system.

4. The system of claim 1, wherein:
    the second structure comprises a translational column; and
    the calculated motion comprises a movement of the translational column to adjust a height of the first structure.

5. The system of claim 4, wherein the processor is further configured to: stop movement of the first structure in the first direction when a position of the translational column reaches a preset limit.

6. The system of claim 1, further comprising:
    a third structure coupling the manipulator to the first structure,
    wherein the processor is further configured to: enter the first mode from a second mode, wherein in the second mode, one or more joints of the third structure are commanded to be in a state that facilitates external manipulation.

7. The system of claim 1, wherein the processor is further configured to: enter the first mode in response to a system joint reaching a range of motion limit, the system joint being a joint of the manipulator or a joint of a third structure coupling the manipulator to the first structure.

8. The system of claim 1, wherein the processor is further configured to: enter the first mode in response to a system joint remaining at or past a range of motion limit for at least a predetermined duration of time, the system joint being a joint of the manipulator or a joint of a third structure coupling the manipulator to the first structure.

9. A method of operating a system comprising a first structure, a manipulator supported by the first structure, a second structure supporting the first structure, and a processor, the method comprising:
    in response to entering a first mode, determining, by the processor and relative to the first structure, a first position of a reference location at a time of entry into the first mode, the reference location being associated with a link of the manipulator supported by the first structure; and
    while in the first mode:
        detecting, by the processor, a manual movement of the reference location to a second position relative to the first structure, wherein a difference between the first position and the second position comprises a displacement having at least a first displacement component in a first direction and a second displacement component in a second direction, the second direction different from the first direction;

calculating, by the processor in response to detecting the manual movement and based on at least the first displacement component, a motion of the second structure that reduces the first displacement component while not changing the second displacement component by causing the first structure to move relative to the reference location in the first direction; and commanding, by the processor, the second structure to move in accordance with the calculated motion.

10. The method of claim 9, wherein the first direction is orthogonal to the second direction.

11. The method of claim 9, wherein:
the second structure comprises a translational column; and
the calculated motion comprises a movement of the translational column to adjust a height of the first structure.

12. The method of claim 9, further comprising entering the first mode from a second mode, wherein in the second mode, one or more joints of a third structure are commanded to be in a state that facilitates external manipulation, and wherein the third structure couples the manipulator to the first structure.

13. The method of claim 9, further comprising:
entering the first mode in response to a joint reaching a range of motion limit, the joint being a joint of the manipulator or a joint of a third structure coupling the manipulator to the first structure.

14. The method of claim 9, further comprising:
entering the first mode in response to a system joint remaining at or past a range of motion limit for a predetermined duration of time, the system joint being a joint of the manipulator or the joint of a third structure coupling the manipulator to the first structure.

15. A non-transitory machine-readable medium having stored thereon a plurality of instructions which when executed by a processor of a system are adapted to cause the processor to perform a method comprising:
in response to entering a first mode, determining relative to a first structure, a first position of a reference location at a time of entry into the first mode, the reference location being associated with a link of a manipulator supported by the first structure; and while in the first mode:
detecting a manual movement of the reference location to a second position relative to the first structure, wherein a difference between the first position and the second position comprises a displacement having a first displacement component in at least a first direction and a second displacement component in a second direction different from the first direction;

calculating, in response to the detected manual movement and based on at least the first displacement component, a motion of a second structure that reduces the first displacement component while not changing the second displacement component by causing the first structure to move relative to the reference location in the first direction; and commanding the second structure to move in accordance with the calculated motion.

16. The non-transitory machine-readable medium of claim 15, wherein the first direction is orthogonal to the second direction.

17. The non-transitory machine-readable medium of claim 15, wherein the first direction is a vertical z-direction of the system.

18. The non-transitory machine-readable medium of claim 15, wherein:
the second structure comprises a translational column; and
the calculated motion comprises a movement of the translational column to adjust a height of the first structure.

19. The non-transitory machine-readable medium of claim 15, wherein the method further comprises entering the first mode from a second mode, wherein in the second mode, one or more joints of a third structure are commanded to be in a state that facilitates external manipulation, wherein the third structure couples the manipulator to the first structure.

20. The non-transitory machine-readable medium of claim 15, wherein the method further comprises:
entering the first mode in response to a system joint reaching a range of motion limit, the system joint being a joint of the manipulator or a joint of a third structure coupling the manipulator to the first structure; or
entering the first mode in response to the system joint remaining at or past the range of motion limit for at least a predetermined duration of time, the system joint being the joint of the manipulator or the joint of the third structure.

* * * * *

UNITED STATES PATENT AND TRADEMARK OFFICE
CERTIFICATE OF CORRECTION

| | | |
|---|---|---|
| PATENT NO. | : 11,723,733 B2 | Page 1 of 1 |
| APPLICATION NO. | : 17/321115 | |
| DATED | : August 15, 2023 | |
| INVENTOR(S) | : Paul G. Griffiths et al. | |

It is certified that error appears in the above-identified patent and that said Letters Patent is hereby corrected as shown below:

On the Title Page

Item (63) Related U.S. Application Data:
Please delete "Continuation of application No. 16/355,517, filed on Mar. 15, 2019, now Pat. No. 11,033,345, which is a continuation of application No. 15/118,305, filed as application No. PCT/US2015/016616 on Feb. 19, 2015, now Pat. No. 10,285,764." and insert --Continuation of application No. 16/355,517, filed on Mar. 15, 2019, now Pat. No. 11,033,345, which is a continuation of application No. 15/118,305, filed on Aug. 11, 2016, now Pat. No. 10,285,764, which is a 371 of application No. PCT/US2015/016616, filed on Feb. 19, 2015.--.

Signed and Sealed this
Fourteenth Day of November, 2023

*Katherine Kelly Vidal*

Katherine Kelly Vidal
*Director of the United States Patent and Trademark Office*